(12) United States Patent
Ingenito

(10) Patent No.: US 7,819,908 B2
(45) Date of Patent: *Oct. 26, 2010

(54) COMPOSITIONS AND METHODS FOR REDUCING LUNG VOLUME

(75) Inventor: Edward P. Ingenito, Kingston, MA (US)

(73) Assignee: Aeris Therapeutics, Inc., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/016,548

(22) Filed: Dec. 17, 2004

(65) Prior Publication Data

US 2005/0244401 A1 Nov. 3, 2005

Related U.S. Application Data

(63) Continuation-in-part of application No. 10/464,115, filed on Jun. 17, 2003, and a continuation-in-part of application No. PCT/US03/19339, filed on Jun. 17, 2003.

(60) Provisional application No. 60/389,731, filed on Jun. 17, 2002, provisional application No. 60/530,832, filed on Dec. 17, 2003.

(51) Int. Cl.
*A61N 1/39* (2006.01)

(52) U.S. Cl. .................. 607/1; 601/2; 604/22; 606/27; 606/32; 607/2; 607/96

(58) Field of Classification Search .............. 424/94.64, 424/94.67, 94.1; 604/514
See application file for complete search history.

(56) References Cited

U.S. PATENT DOCUMENTS

| 5,714,470 | A | * | 2/1998 | Peet et al. | 514/17 |
| 5,780,440 | A | * | 7/1998 | Lezdey et al. | 514/21 |
| 6,001,814 | A | * | 12/1999 | Gyorkos et al. | 514/18 |
| 6,123,663 | A | | 9/2000 | Rebuffat | |
| 6,200,333 | B1 | * | 3/2001 | Laufer | 607/96 |
| 6,287,290 | B1 | * | 9/2001 | Perkins et al. | 604/516 |
| 6,458,387 | B1 | * | 10/2002 | Scott et al. | 424/489 |
| 6,610,043 | B1 | * | 8/2003 | Ingenito | 604/514 |
| 6,682,520 | B2 | * | 1/2004 | Ingenito | 604/514 |

FOREIGN PATENT DOCUMENTS

WO WO 01/10314 A2 * 2/2001

OTHER PUBLICATIONS

Varoli et al., The society of Thoracic surgeons, 1998, vol. 65, p. 807-809.*
Daniel et al., Annals of Surgery, 1996, vol. 223, No. 5, p. 526-531.*
American Academy of Pediatrics, Committee on Fetus and Newborn, Pediatrics, 1999, vol. 103, p. 684-685.*
Golab et al., British Journal of Cancer, 2000, vol. 82, No. 8, p. 1485-1491.*
Drummond et al., Pharmacological Reviews, 1999, vol. 51, No. 4, p. 692-743.*
Coyle et al., J Clin. Invest, 1995, vol. 95, p. 1735-1740.*
Witkowski et al., Clinics in Dermatology, 1996, vol. 14, p. 89-93.*
Ayorinde et al., Rapid communications in Mass Spectrometry, 2000, vol. 14, p. 2116-2124.*
Kurohane et al., Cancer Letters, 2001, vol. 16, p. 49-56.*
Coyle et al. , J Clin. Invest, 1995, vol. 95, p. 1735-1740.*
Daffertshofer et al., European Journal of Ultrasound 2002, vol. 16, p. 121-130.*
O'Brien et al., J. Acoust. Soc. Am., 111, No. 12, p. 1102-1109.*
Bonney, et al. "Pharmacological Profile of the Substituted Beta-Lactam L-659,286: A Member of a New Class of Human PMN Elastase Inhibitors," *J. of Cellular Biochemistry* 1989, 39, 47-53.
Brunt, et al. "Inactivation of Surfactant in Rat Lungs," *Pediatric Research* 1996, 39(2), 1-8.
Kjaergard, et al. "Prevention of Air Leakage by Spraying Vivostat Fibrin Sealant After Lung Resection in Pigs," *Chest* 2000, 117, 1124-1127.
Richards, et al. "Isolation, Biochemical Characterization, and Culture of Lung Type II Cells of the Rat," *Lung* 1987, 165, 143-158.
Wencker, et al. "Longitudinal Follow-up of Patients with alphal-Protease Inhibitor Deficiency Before and During Therapy with IV-alpha1-Protease Inhibitor," *Chest* 2001, 119(3), 737-744.

* cited by examiner

*Primary Examiner*—Leon B Lankford
*Assistant Examiner*—Kade Ariani
(74) *Attorney, Agent, or Firm*—Foley Hoag LLP

(57) ABSTRACT

The invention includes a method for performing non-surgical lung volume reduction in a patient by applying an amount of energy with a catheter to a diseased alveolar region of the lung of a patient having emphysema, wherein the amount of energy is sufficient to damage the epithelial cells and the epithelial barrier within the diseased alveolar region of the lung and collapse at least a portion of said region thereby reducing the lung volume, and wherein the energy comprises thermal energy, electrical energy, and ultrasonic energy.

7 Claims, 20 Drawing Sheets

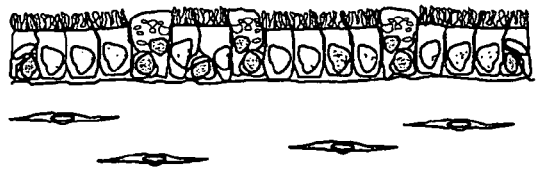 Airway Epithelial Surface Pre-Treatment Surface Epithelial Cells with Underlying Fibroblasts Removal of Epithelial Cells by Enzymatic Exposure

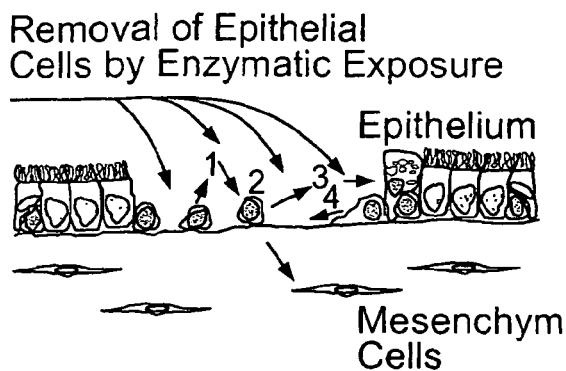 Subsequent Hydrogel Instillation Stimulates Mesenchymal Cells in the Interstitium to Migrate into the Airway Lumen and Promote Scan Formation

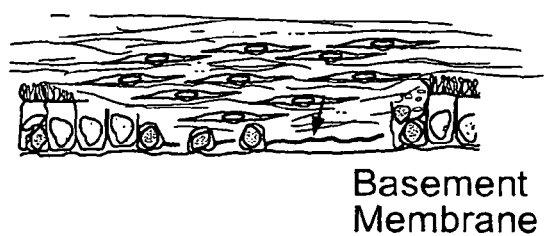 Chemotaxis of Fibroblasts and Subsequent Collagen Deposition Leads to Scarring and Permanent Collapse in Target Region in a Controlled Safe Fashion.

FIG. 10

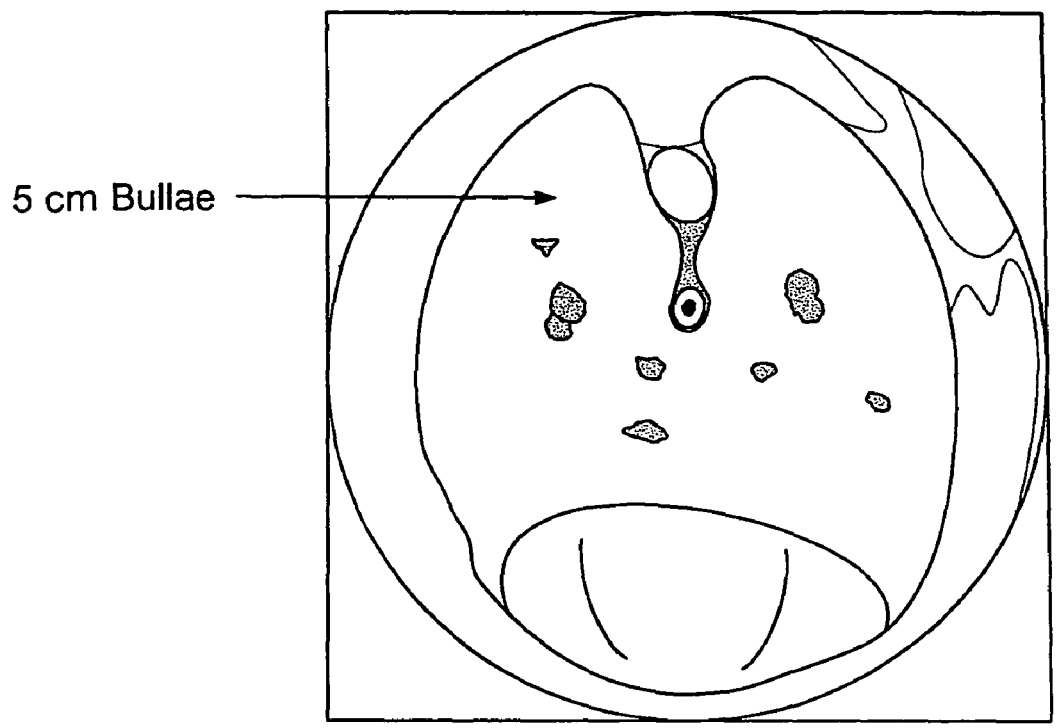
5 cm Bullae
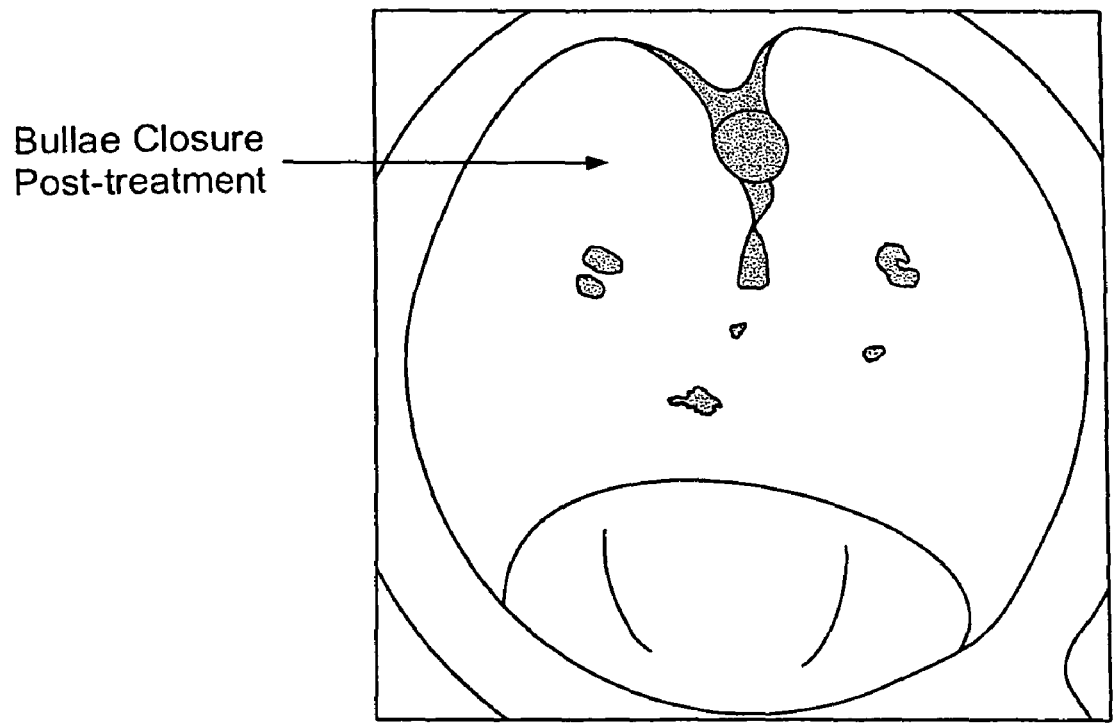
Bullae Closure Post-treatment
FIG. 14B

|  | FRC (Liters) | TLC (Liters) | RV (Liters) | VC (Liters) |
|---|---|---|---|---|
| Baseline | 1.71 ± 0.23 | 3.22 ± 0.35 | 1.01 ± 0.54 | 2.21 ± 0.35 |
| Emphysema | 2.04 ± 0.26 | 3.41 ± 0.42 | 1.43 ± 0.21 | 1.98 ± 0.44 |
| Post BVR-1 | 1.65 ± 0.37 | 2.92 ± 0.43 | 0.64 ± 0.33 | 2.28 ± 0.39 |
| Post BVR-3 | 1.74 ± 0.42 | 3.00 ± 0.41 | 0.81 ± 0.36 | 2.19 ± 0.46 |

FIG. 15

COMPOSITIONS AND METHODS FOR REDUCING LUNG VOLUME

RELATED APPLICATIONS

This application claims priority to and is a continuation-in-part of U.S. Ser. No. 10/464,115 filed on Jun. 17, 2003, which claims benefit under 35 U.S.C. §119(e) of the priority date of U.S. Provisional Application No. 60/389,731, filed Jun. 17, 2002. This application also claims priority to and is a continuation-in-part of PCT US03/19339 filed on Jun. 17, 2003, which claims priority to U.S. Provisional Application No. 60/389,731, filed Jun. 17, 2002. This application also claims benefit under 35 U.S.C. §119(e) of the priority date of U.S. Provisional Application No. 60/530,832, filed Dec. 17, 2003. The disclosures of all of the above applications are incorporated herein by reference in their entirety.

FIELD OF THE INVENTION

This invention features compositions and methods for treating patients who have certain lung diseases, such as emphysema.

BACKGROUND

Emphysema, together with asthma and chronic bronchitis, represent a disease complex known as chronic obstructive pulmonary disease (COPD). These three diseases are related in that they each cause difficulty breathing and, in most instances, progress over time. There are substantial differences, however, in their etiology, pathology, and prognosis. For example, while asthma and chronic bronchitis are diseases of the airways, emphysema is associated with irreversible, destructive changes in lung parenchyma distal to the terminal bronchioles. Cigarette smoking is the primary cause of emphysema; the smoke triggers an inflammatory response within the lung, which is associated with an activation of both elastase and matrix metalloproteinases (MMPs). These enzymes degrade key proteins that make up the tissue network of the lungs (Shapiro et al., *Am. J. Resp. Crit. Care Med.* 160:s29-s32, 1999; Hautamaki et al., *Science* 277:2002-2004, 1997). In fact, the pathological determinant of lung dysfunction in emphysema is the progressive destruction of elastic tissue, which causes loss of lung recoil and progressive hyper-expansion.

Almost two million Americans and at least three times that many individuals worldwide suffer from emphysema (see American Thoracic Society, *Am. J. Resp. Crit. Care Med.* 152:s77-s121, 1995). The average patient with emphysema reaches a critical level of compromise by about the age of 60 and, at that point, often begins to experience symptoms such as shortness of breath. In addition, functional capacity becomes reduced, quality of life is compromised, and the frequency of hospitalization is increased. Despite aggressive public health initiatives, cigarette smoking remains common, and emphysema will likely remain a major public health problem well into the new millennium.

Even though emphysema is a distinct condition, the therapies that have been developed to treat it are patterned after those used to treat asthma and chronic bronchitis. The treatments can be grouped into five categories: (1) inhaled and oral medications that help open narrowed or constricted airways by promoting airway muscle relaxation; (2) inhaled and oral medications that reduce airway inflammation and secretions; (3) oxygen therapy, which is designed to delay or prevent the development of pulmonary hypertension and cor pulmonale (right ventricular failure) in patients with chronic hypoxemia; (4) exercise programs that improve cardiovascular function, functional capacity, and quality of life; and (5) smoking cessation programs to delay the loss of lung function by preventing progression of smoking-related damage (Camilli et al., *Am. Rev. Resp. Dis.* 135:794-799, 1987). Although each of these approaches has been shown to have beneficial effects in this patient population, only oxygen therapy and smoking cessation significantly alter the natural history of this disease (Nocturnal Oxygen Therapy Trial Group, *Ann. Intern. Med.* 93:391, 1980).

Surgical therapy has recently been introduced as an adjunct to the medical treatments described above, and the results have been impressive. The surgical approach, known as lung volume reduction surgery (LVRS), improves lung function, exercise capacity, breathing symptoms, and quality of life in the majority of emphysema patients who meet designated selection criteria (Cooper et al., *J. Thorac. Cardiovasc. Surg.* 109:106-116, 1995). In LVRS, damaged, hyper-inflated lung is removed, and this is believed to provide a better fit between the over-expanded lung and the more normal sized chest wall. The fraction of the lung that remains within the chest cavity can better expand, and this increases the proportion of lung that can effectively contribute to ventilation (Fessler et al., *Am. J. Resp. Crit. Care Med.* 157:715-722, 1998). Recoil pressures increase, and expiratory flows improve. To date, LVRS is the only treatment that directly addresses lung hyper-expansion, which is the primary physiological abnormality of emphysema. Unfortunately, the benefits of LVRS may tend to decline over time (see Gelb et al., *Am. J. Resp. Crit. Care Med.* 163:1562-1566, 2001).

SUMMARY

We have discovered that lung volume reduction, a procedure that reduces lung size by removing damaged (e.g., over-expanded) regions of the lung, can be accomplished by procedures carried out through the patient's trachea (e.g., by inserting devices and substances through a bronchoscope), rather than by procedures that disrupt the integrity of the chest wall (Ingenito et al., *Am. J. Resp. Crit. Care Med.* 164:295-301, 2001; Ingenito et al., *Am. J. Resp. Crit. Care Med.* 161:A750, 2000; Ingenito et al., *Am. J. Resp. Crit. Care Med.* 163:A957, 2001). We have also discovered that the methods for lung volume reduction (particularly non-surgical LVR) can be improved by damaging the epithelial cells that line the inner surface of the lung. The term "damaging" encompasses any activity that renders the population of epithelial cells less than fully or normally functional. For example, "damaging" can be achieved by disrupting, destroying, removing or ablating cells within this population (mechanically or non-mechanically (e.g., by inducing cell death)) or by otherwise rendering the cells within the epithelium less than fully functional. In one embodiment, the epithelial cells are selectively damaged (i.e., affected to an extent greater than, and maybe much greater than, non-epithelial cells). While the methods of the present invention are not limited to those in which any particular cellular event occurs (or fails to occur), we believe that compositions and methods of the invention may be most useful or successful when they inhibit one or more of the functions normally carried out by the lung epithelium. For example, compositions and methods described herein may inhibit the ability of epithelial cells to regulate fluid passage between blood vessels and the alveolar compartment; to produce. surfactant, which is critical for maintaining alveolar patency; or to serve as a barrier between the alveolar compartment and the underlying lung interstitium. While such functions help maintain homeostasis within the normal lung, we have discovered that they can hinder effective lung volume reduction (e.g., BLVR), where one aims to achieve or control scar formation. Scarring is facilitated by interstitial fibroblasts that reside beneath the epithelial surface and produce collagen. Our studies have shown that eliminating the epithelial barrier in a targeted area of the lung, in whole or in part, improves the efficacy of LVR (e.g., BLVR).

Accordingly, aspects of the present invention include methods for damaging epithelial cells within tissues, such as the lung. In some embodiments, the epithelial cells may impede a process mediated by non-epithelial cells (e.g., in the lung, epithelial cells may impede scarring, which is mediated, at least in part, by fibroblasts and which is desirable in some cases (e.g., in lung volume reduction)). Thus, methods of the invention, or the use of compositions described herein, can be used in any circumstance where one wishes to promote scarring or adhesion between two tissues (whether in the context of volume reduction in the lung, or to promote adhesion between damaged (e.g., traumatized) tissue in the lung or elsewhere). Epithelial cells can be damaged by administration of an enzyme, but this is far from the only means by which they can be damaged; methods of the invention can be practiced by administering other types of agents or by applying a force that damages epithelial cells. For example, in addition to, or instead of, administering an enzyme, one could administer a detergent, a pro-apoptotic agent (e.g. ceramide or ceramide-6-phosphate), a photo-sensitizing agent, or some form of energy. For example, one could apply mechanical energy through small cytologic brushes; thermal energy (in the form of heat or cold); or ultrasonic energy. These methods are described further below. As noted above, regardless of the way in which the damage is caused, it can be selective (i.e., it can damage one cell type (e.g., epithelial cells) more than another cell type (e.g., a fibroblast or other non-epithelial cell); it can damage some, but not all, of the targeted cells (and, possibly, some non-targeted cells); or it can damage essentially all of the targeted cells to a limited extent), and it can be characterized in several ways (e.g., as selective ablation, controlled shedding, cellular disruption, etc.). Also, in some aspects of the invention, a polycationic composition may be used to damage epithelial cells. In one embodiment, one or more polycationic compositions may be included with one or more other cell-disrupting compositions described herein. In one embodiment, one or more polycationic compositions may be included with an adhesive composition.

As methods for damaging the epithelial cell lining can be carried out as part of a lung volume reduction procedure, aspects of the invention also include methods of reducing lung volume by administering, to a patient (which includes but is not limited to human patients; domesticated animals including, but not limited to, pigs, cows, horses, sheep, goats, dogs, cats, mice, cats, and other farm animals or pets also may be treated), an agent that damages epithelial cells, and compositions (e.g., physiologically acceptable compositions comprising one or more such agents) are also within the scope of the present invention. No special meaning is attached to the term "agent." Unless otherwise noted, it is interchangeable with other terms such as "substance" or "compound," and it can be biologically active (such as an enzyme) or inactive (such as a compound that is inert until activated by subsequent application of, for example, heat, cold, or some form of light; the substance can also be a prodrug). More specifically, the substance can be an enzyme (e.g., a protease such as a serine protease such as trypsin, chymotrypsin, elastase, or a matrix metalloproteinase; mixtures of enzymes can also be used). Thus, in one embodiment, the invention features a method of reducing lung volume by administering, through the patient's trachea, a composition comprising an enzyme. This step can be followed (immediately or after one or more intervening steps which may serve to contain or limit the enzyme's activity) by a procedure that induces collapse of a region of the lung in which epithelial cells have been damaged (exemplary intermediate steps are described below). For example, one can induce collapse by administering a material that increases the surface tension of fluids lining the alveoli (i.e., a material that acts as an anti-surfactant). This material can be introduced through a bronchoscope (preferably, through a catheter or similar device lying within the bronchoscope), and it can include fibrinogen, fibrin (e.g., a fibrin I monomer, a fibrin II monomer, a des BB fibrin monomer, or any mixture or combination thereof), or biologically active mutants (e.g., fragments) thereof. In the event fibrinogen is selected as the anti-surfactant, one can promote adhesion between collapsed areas of the lung by exposing the fibrinogen to a fibrinogen activator, such as thrombin (or a biologically active variant thereof), which cleaves fibrinogen and polymerizes the resulting fibrin. Other substances, including thrombin receptor agonists and batroxobin, can also be used to activate fibrinogen. If fibrin is selected as the anti-surfactant, no additional substance need be administered; fibrin can polymerize spontaneously, thereby adhering one portion of the collapsed tissue to another. However, other adhesive and/or surfactant compositions may be used as described herein.

When the tissue in question is lung tissue, tissue collapse can also be induced by impeding airflow into and out of the region of the lung that is targeted for collapse. This can be achieved by inserting a balloon catheter through, for example, a bronchoscope and inflating the balloon so that it occludes the bronchus or bronchiole into which the balloon portion of the catheter has been placed. Devices other than a balloon catheter may also be used so long as they can be maneuvered into the desired location within the respiratory tract and they can create a barrier that impedes airflow to alveoli (or any portion of the lung distal to the occlusion). The barrier can be temporary (i.e., sustained only as long as is necessary for distal lung tissue to collapse) or more permanent (e.g., a plug of degradable or non-degradable material). In one embodiment, the barrier may be a stent or a valve.

Any of the compositions administered to the patient (e.g., an enzyme-containing solution an anti-surfactant, a detergent, a polycation-containing solution, etc.) can also contain one or more antibiotics to help prevent infection. Alternatively, or in addition, antibiotics can be administered via other routes (e.g., they may be administered orally or intramuscularly). Any of the compositions administered to the patient can also be included in a kit. For example, aspects of the invention include kits that include an enzyme-containing preparation (e.g., a physiologically acceptable solution that contains one or more serine proteases) and/or a preparation to inhibit the activity of the protease (e.g., a physiologically acceptable solution that contains serum or a neutralizing antibody) and/or a preparation to induce lung collapse (e.g., a physiologically acceptable solution that contains an anti-surfactant) and/or an antibiotic. Other aspects of the invention include kits containing one or more detergents; one or more polycation-containing solutions; one or more biological or synthetic adesive solutions (e.g. one or more biological or synthetic hydrogel solutions) or any combination thereof. These preparations can be formulated in accordance with the information provided further below and with knowledge generally available to those who routinely develop such preparations. The preparations can be sterile or contained within vials or ampules (or the like; in solution or in a lyophilized form)

that can be sterilized, and the preparations can be packaged with directions for their preparation (if required) and use. In one embodiment, a kit containing one or more of the preparations just described may be useful to damage epithelial cells within the lung prior to a lung volume reduction procedure. In one embodiment, a kit may be useful to damage epithelial cells within a lung during a lung volume reduction procedure. One or more enzymes, preparations that inhibit the enzyme's activity can also be packaged with other agents. For example, they can be packaged with nucleic acids (those that encode polypeptides, antisense oligonucleotides, or an siRNA) that can be used to transfect mesenchymal or other cell types remaining within the lung after the epithelial cells have been damaged, or with other therapeutic agents (e.g., polypeptides or small molecules). Aspects of the invention also include kits that would be used when one wishes to condition the lung in other ways. For example, where one wishes to use a photodynamic therapy, the kit can contain liposomes and a photodynamic agent such as photofrin (liposome-encapsulated photodynamic agents per se are also within the scope of the invention); where one wishes to use a mechanical device, the kit may contain a cytology brush configured to extend to and remove epithelial cells from a targeted region of the respiratory tract (the brush per se is also within the scope of the invention); where one wishes to use ultrasonic energy, the kit may contain a perfluorocarbon; and where one wishes to use electric energy, the kit may contain an electrolyte solution to improve energy conduction and a rinsing agent to dilute the electrolyte solution after use. A kit can also include a detergent a buffer, a wash solution, etc. Any of these kits can contain devices used in non-surgical lung volume reduction. For example, they can also contain a catheter (e.g., a single- or multi-lumen (e.g., dual-lumen) catheter that, optionally, includes a balloon or other device suitable for inhibiting airflow within the respiratory tract), tubing or other conduits for removing material (e.g., solutions, including those that carry debrided epithelial cells) from the lung, a stent or a valve or other device that may be placed in an airway to block or reduce airflow into or out of a lung or lung region, and/or a bronchoscope.

As with the enzyme-containing kits, those designed to condition the epithelium in other ways can include agents useful in procedures other than lung volume reduction. For example, they can contain nucleic acids (those that encode polypeptides, antisense oligonucleotides, or an siRNA) that can be used to transfect mesenchymal or other cell types remaining within the lung after the epithelial cells have been damaged, or other therapeutic agents (e.g., polypeptides or small molecules).

Methods in which epithelial cells are damaged can also be carried out as part of other therapeutic regimes. They can be carried out, for example, when one wishes to deliver a therapeutic agent (e.g., a nucleic acid molecule, a protein, or a chemical compound (e.g., a small molecule)) to cells that lie beneath (or are otherwise obscured by) epithelial cells. Accordingly, aspects of the invention include methods of delivering a therapeutic agent to a cell within a patient, wherein the cell is a non-epithelial cell that lies beneath an epithelial cell layer, or is otherwise obscured by an epithelial cell. The methods can be carried out by, first, damaging the epithelial cells by any of the methods, mechanical or non-mechanical, described herein and, second, administering a therapeutic agent to the region where the epithelial cells were damaged. The damage can include destroying, or removing epithelial cells and the destruction or removal may be selective (i.e., the epithelial cells are affected to an extent greater than, and preferably much greater than, non-epithelial cells are affected). The step in which a therapeutic agent is administered can be carried out by any method known in the art. When epithelial cells are damaged or removed in preparation for delivering a therapeutic agent (including one or more agents that induce lung collapse, and/or adhesion of one portion of a collapsed lung region to another; and/or fibrosis in or around a collapsed lung region, as part of a lung volume reduction procedure), the extent of the damage to the epithelial cells can vary. It is not necessary to destroy all epithelial cells. The method will be considered a success so long as the outcome is better than the outcome reasonably expected without any epithelial cell ablation or damage.

More specifically, the invention includes methods for performing non-surgical lung volume reduction in a patient by (a) administering, through the patient's trachea, a composition comprising an enzyme (e.g., a protease, such as a serine protease (e.g., trypsin, chymotrypsin, elastase, or an MMP), and/or a detergent, and/or a polycation; and (b) collapsing a region of the lung, at least a portion of which was contacted by the composition administered in step (a). The patient can have COPD (e.g., emphysema) or their lung can be damaged by a traumatic event. The tissue in the targeted area can also include an abscess or fistula. One can similarly treat other tissues (i.e., non-lung tissues) by exposing those tissues to an enzyme-containing composition (or other composition described herein). These tissues may be those that are obscured from a therapeutic agent by epithelial cells or that will contact an implantable device. Where the lung is targeted, one can collapse a region of the lung by administering, to the targeted region, a substance that increases the surface tension of fluids lining the alveoli in the targeted region, the surface tension being increased to the point where the region of the lung collapses. The concentration of the active agents in the compositions of the invention are described further below, but we note here that the concentrations will be sufficient to damage the epithelial cell lining of the lung or the epithelium lining or otherwise covering another tissue. The compositions described herein can be used not only for lung volume reduction and other tissue treatments, but also for use as medicaments, or for use in the preparation of medicaments, for treating patients who have a disease or condition that would benefit from selective epithelial damage and subsequent fibrosis or scar formation (e.g., a disease or condition in which the target cells would otherwise be obscured by the epithelial lining of a tissue or one that can be treated with an implanted device (e.g., a stent or a valve, pump, or prosthetic device)).

The details of one or more embodiments of the invention are set forth in the accompanying drawings and the description below. Other features, objects, and, advantages of the invention will be apparent from the description and drawings, and from the claims.

BRIEF DESCRIPTION OF THE DRAWINGS

FIG. 1A illustrates insertion of a device in which an elongated flexible member (e.g., a wire or cable) is attached to a brush that is guided through a bronchoscope into a region of a patient's respiratory tract that is targeted for reduction. The brush shown here has unidirectional bristles to facilitate removing epithelial cells. FIG. 1B illustrates the juxtaposition between the brush and the epithelial cells in more detail before (left-hand panel) and after (right-hand panel) the cells are treated. Fibroblasts lie beneath an epithelial cell layer that is contacted by the brush. As the brush is withdrawn (and it may be inserted and withdrawn over a region several times (i.e., the procedure may involve a scrubbing-type action)) the bristles damage and/or remove the epithelial cells. As a result, epithelial cells are dislodged and may become trapped in the bristles of the brush. The epithelial cell layer is then wholly or partially denuded.

FIG. 2A illustrates insertion of a balloon-tip dual lumen catheter through a bronchoscope to a region of the patient's lung that is targeted for reduction. When the balloon is inflated, it isolates the target region. The catheter and the target region of the lung contain a medium such as a perfluorocarbon (PFC) medium. FIG. 2B illustrates the application of ultrasonic energy in more detail. An ultrasonic generator is attached to the proximal end of the PFC-filled catheter, and ultrasound energy is transmitted to the epithelial cell layer (left-hand panel). Following application of the ultrasonic energy (right-hand panel), the epithelial cell layer is denuded. Detached cells and the PFC medium can be removed by suction (e.g., a suction tube can be inserted through the second of the two lumens in the dual lumen catheter). This method, or any of the others for damaging epithelial cells, may be done to condition a region of the lung prior to lung volume-reduction or prior to administering a therapeutic agent to cells beneath the epithelial layer.

FIG. 3A illustrates insertion of an insulated cryocatheter, through which one can administer cold nitrogen gas to a region of the patient's lung that is targeted for reduction. When the balloon is inflated, it isolates the target region. Suction may be applied for a time sufficient to degas the region (e.g., 3-4 minutes) before the $N_2$ is applied, and the process may be repeated (i.e., the tissue may be thawed or allowed to thaw before $N_2$ is again applied). FIG. 3B illustrates the application of cold gas in more detail (left-hand panel). Epithelial cells detach following the freeze-thaw process (right-hand panel).

FIG. 4A illustrates an expansion tipped unipolar electrode catheter positioned within a selected (or target) region of the lung. A solution containing electrolytes (an "electrolyte rinse solution") can be placed in the targeted region of the lung to improve energy conduction distal to the electrode. The structure of the catheter is shown in more detail in FIG. 4B. A wire is contained within the flexible shaft of the catheter and an electrode resides at or near the tip. The arrows within the airways represent energy transmitted from a power source and through the rinse solution (left-hand panel). The epithelial cell layer is damaged when electrical energy is applied; some of the epithelial cells that are dislodged are shown within the airway (right-hand panel). These cells can be removed by removing the rinse solution (e.g., with a suction device inserted through the bronchoscope or a lumen of the catheter).

FIG. 5A illustrates a balloon-tipped dual lumen catheter positioned within a targeted region of the lung. A PDT-compatible solution, such as one containing liposomes and photofrin, is contained within the target region. To activate the photofrin and damage epithelial cells, a light-emitting fiber is extended through a lumen of the catheter (FIG. 5B, left-hand panel). The epithelial cells that slough away from the layer of epithelial cells can be removed by removing the photofrin solution (e.g., with a suction device inserted through the bronchoscope or a lumen of the catheter). (Not shown here but also within the scope of the present invention is pretreatment using systemic application of photofrin rather than the liposomal photofrin solution.)

FIG. 6A illustrates a single lumen catheter (although a multi-lumen catheter can also be used), inserted through an instrumentation (or "working") channel of a bronchoscope and into the target region of the lung. A balloon inflated at the distal tip of the catheter seals the target region. The enzyme-containing solution is applied first and a solution containing a substance that inhibits the activity of the enzyme may be applied subsequently (FIG. 6B, left-hand panel). Epithelial cells that are sloughed off may be removed by lavage after either the enzyme-containing solution or the neutralizing solution is applied (FIG. 6B, right-hand panel).

FIG. 10 is a series of drawings showing the effect of enzyme pre-conditioning on epithelial cells within the lung. The top panel illustrates the epithelial surface in cross-section in an untreated animal. Fibroblasts lie beneath the epithelial cell layer. The middle panel illustrates a disruption in the epithelial cell layer, resulting from exposure to an enzyme. Subsequently (e.g., after application of a hydrogel), mesenchymal cells can migrate into the airway lumen and promote scar formation. As shown in the bottom panel, chemotaxis of fibroblasts and subsequent collagen deposition leads to scarring of the target region, which secures the area of collapse.

FIGS. 14A and 14B are images of the respiratory system at various times. FIG. 14A shows a CT scan of an animal with heterogeneous emphysema, with a bullous lesion developed in response to papain instilled bronchoscopically (left-hand panel). The bullae in the right upper dorsal lobe measured 5×3×7 cm before treatment. After enzyme pre-conditioning and BVR (right-hand panel), the lesion was reduced in size to 3×2×2 cm. FIG. 14B shows a CT scan of an animal with heterogeneous emphysema, with a 5 cm bullae (upper panel) that was completely closed three months after the BVR procedure was performed (lower panel). In addition, sites of diffuse emphysema treated with BVR are also visible.

FIG. 15 is a Table summarizing the physiological parameters measured in post-BVR studies performed at 1 and 3 months (see the Examples).

DETAILED DESCRIPTION

Figure 1A:
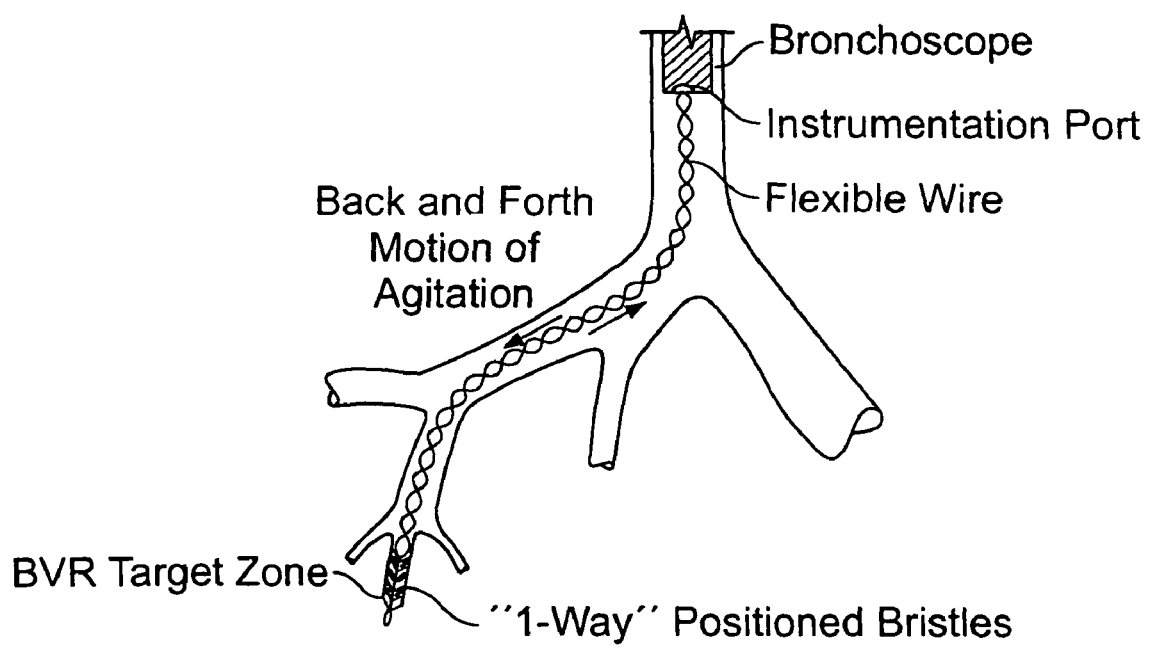
FIGS. 1A and 1B are schematic representations of a mechanical method for damaging epithelial cells, which may be done to condition a region of the lung prior to BVR (bronchoscopic volume reduction) or prior to administering a therapeutic agent to cells beneath the epithelial layer.

Aspects of the present invention include methods that can be used to damage (e.g., to selectively ablate) epithelial cells (e.g., those in an epithelial cell layer) in an organ, such as the lung. The damage can be done in the context of another procedure. For example, it can be done in preparation for reducing the volume of inherently collapsible tissue; in preparation for treatment of cells that would otherwise be obscured by the epithelial lining of a tissue; or in preparation for processes where one epithelial cell-bearing tissue is fused to another or to an implanted device (e.g., a stent or a valve, pump, or prosthetic device). In another embodiment, damage can be done as part of a procedure (as opposed to before the procedure) such as lung volume reduction.

When carried out in the context of lung volume reduction (e.g., non-surgical LVR), methods for effecting epithelial damage can be used to treat patients who have certain diseases of the lung, such as emphysema (a chronic obstructive pulmonary disease (COPD)). While it may seem counterintuitive that respiratory function would be improved by removing part of the lung, excising over-distended tissue (as seen in patients with heterogeneous emphysema) allows adjacent regions of the lung that are more normal to expand. In turn, this expansion allows for improved recoil and gas exchange. Even patients with homogeneous emphysema benefit from LVR because resection of abnormal lung results in overall reduction in lung volumes, an increase in elastic recoil pressures, and a shift in the static compliance curve towards normal (Hoppin, *Am. J. Resp. Crit. Care Med.* 155:520-525, 1997).

BLVR is performed by, for example, collapsing a selected region of the lung and adhering one portion of the collapsed region to another and/or promoting fibrosis or scarring in or around the collapsed and/or adherent tissue. It may be desirable to prepare (or "condition") one or more of the affected regions of the lung or a portion thereof. The conditioning, which promotes fibrosis and can lead to stronger or longer-lasting adhesion between collapsed portions of the tissue, can be carried out in a number of ways. Various methods for conditioning tissue, any of which can be carried out prior to a lung volume reduction (e.g., BLVR) or another of the therapeutic procedures described herein, are described below. Moreover, these methods may be combined. For example, one could use an enzyme and ultrasonic energy to remove epithelial cells from the respiratory tract.

Accordingly, aspects of the invention relate to LVR methods that may include one or more procedures. In one embodiment, a cell-disrupting composition is administered to one or more target lung regions to disrupt the epithelial cells in order to promote fibrosis or scarring upon collapse of the target region(s). A cell-disrupting composition may include one or more enzymes, detergents, polycations, or a combination thereof. A cell-disrupting composition may be introduced one or more times into the target lung regions. After being introduced into a target region, the cell-disrupting composition may be removed (e.g. by suction). In certain embodiments, the target lung region(s) are washed out after being exposed to a cell-disrupting composition in order to prevent excessive damage. In one embodiment, the target region(s) are collapsed during exposure to the cell-disrupting composition. Collapse may be caused by any technique (e.g. by including at least one anti-surfactant in the cell-disrupting composition, by blocking airflow into and out of the target region(s), by sucking air out of the target region(s), by washing away the natural surfactant in the target region(s), etc., or a combination thereof). In one embodiment, a cell-disrupting composition (particularly a non-toxic composition) may be left in a collapsed lung region(s) for a sufficient time to promote fibrosis without requiring a subsequent adhesive composition or a permanent airway occlusion to maintain stable collapse of the target region(s).

In one embodiment, aspects of the invention include administering an adhesive composition to a target lung region in order to adhere collapsed portions of target lung region(s) together to form stabilized collapsed lung region(s). An adhesive composition may be a biological or synthetic adhesive (e.g. a biological or synthetic hydrogel) including those described herein. In one embodiment, an adhesive composition may be administered after exposing a target lung region to a cell-disrupting composition in order to promote fibrosis and or scarring in adhered portions of the lung that contain a damaged epithelial cell layer. In one embodiment, an adhesive composition also may include one or more cell-disrupting agents (e.g. detergents and/or polycations). In one embodiment, an adhesive composition that contains a cell-disrupting agent may be introduced to a target lung region without pre-treating the region with any cell-disrupting composition. The cell-disrupting agent in the adhesive composition may be present in an amount sufficient to disrupt epithelial cells and promote fibrosis or scarring in adhered regions. It should be appreciated that the adhesive composition may be administered under conditions that promote collapse of the target lung region. As discussed above, collapse may be promoted by the presence of an antisurfactant in the adhesive, blocking certain airways, sucking air out of the target region, other techniques or a combination thereof.

According to aspects of the invention, fibrosis or scarring also may be promoted by including one or more growth factors (e.g. polypeptide growth factors and/or other agents that promote fibrosis or scarring) in any one (or all) of the compositions that are administered to a target lung region. For example, a growth factor may be included in an adhesive composition. In some embodiments, a growth factor may be included in a primer solution, particularly when the primer solution may be left in the lung to induce lung volume reduction without adding a subsequent adhesive composition.

According to aspects of the invention, a target region in a lung may be one or more of an alveolus, a bronchiole, an airway, a trachea, different branches of a bronchiolar tree, etc.

or a combination thereof. A target region may be a diseased region with below normal tissue recoil.

Methods that Employ an Enzyme

One can use a preparation (e.g., a physiologically acceptable solution, suspension, or mixture; exemplary formulations are described further below) that contains one or more enzymes to selectively damage epithelial cells (e.g., epithelial cells lining the respiratory tract). Preparations that contain trypsin but lack divalent cations are used in conventional cell culture practice to displace cells, including epithelial cells and fibroblasts, from tissue culture plastic. Such preparations have also been used in situations to prepare primary epithelial cell cultures; they are known as an effective means for removing the epithelial cell layer without causing marked damage to the tissue as a whole.

Figure 6A:
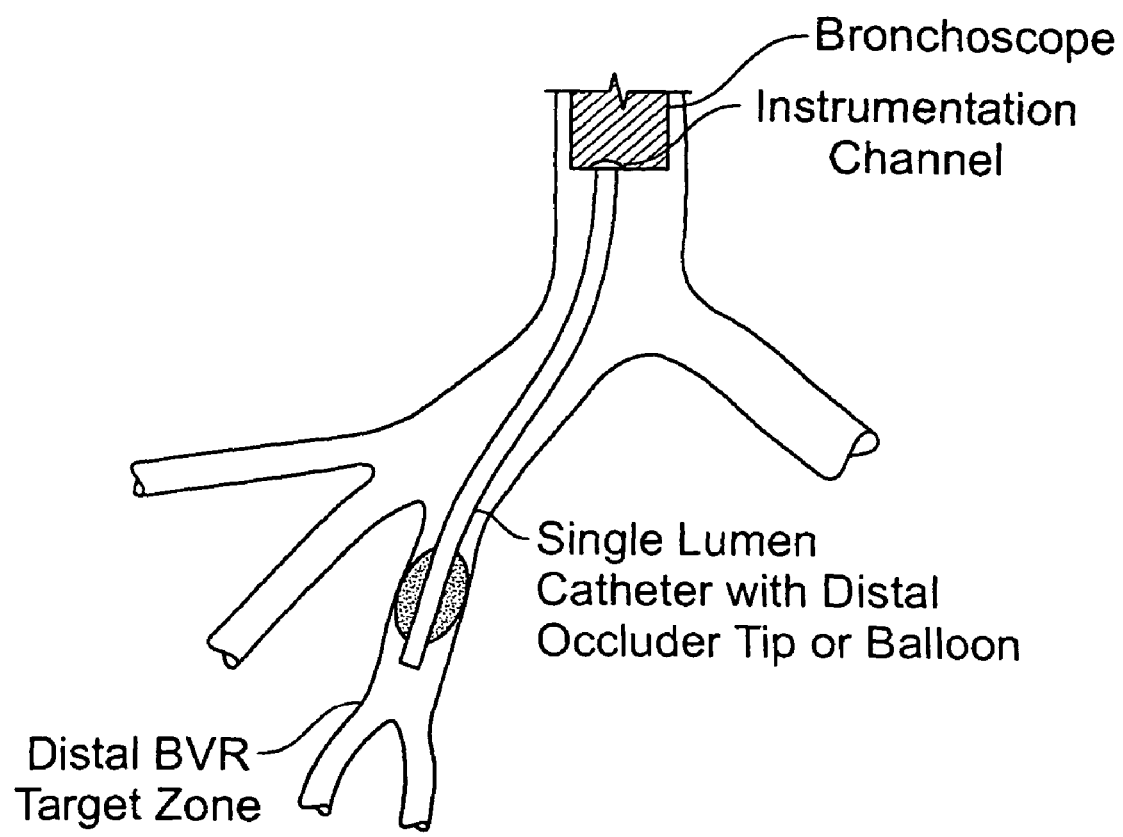
FIGS. 6A and 6B are schematic representations of a method for damaging epithelial cells within the lung using an enzyme-containing solution.
Figure 6B:
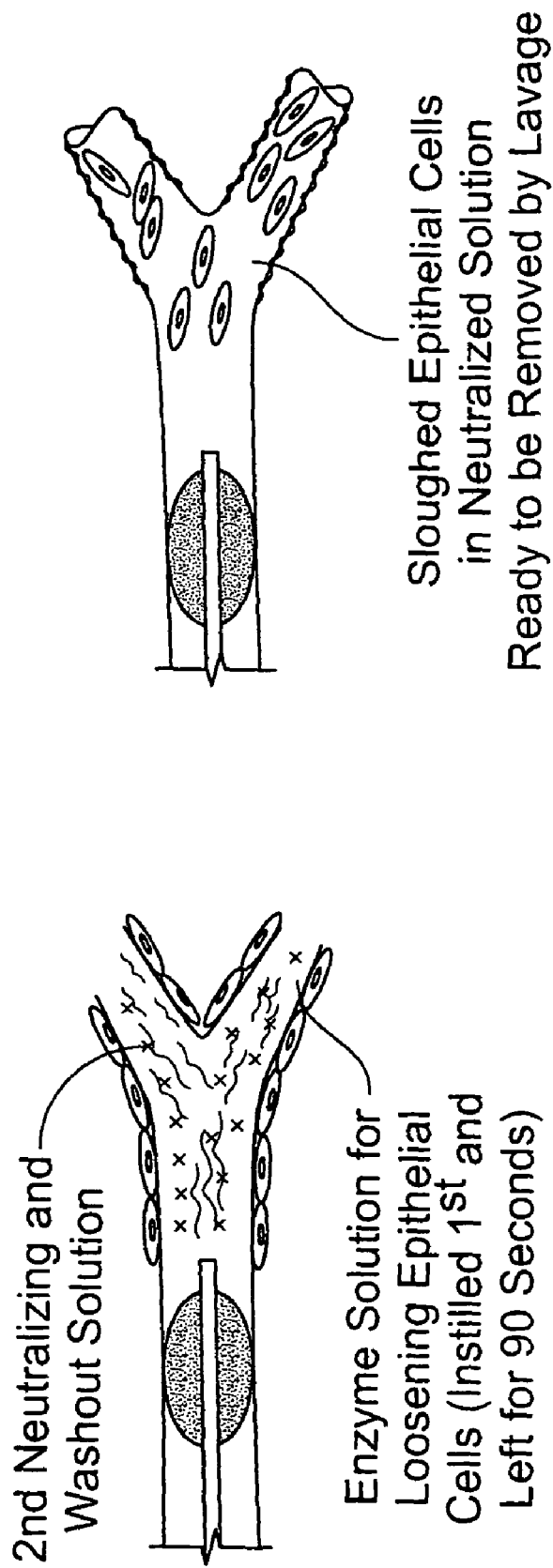
Figure 7:
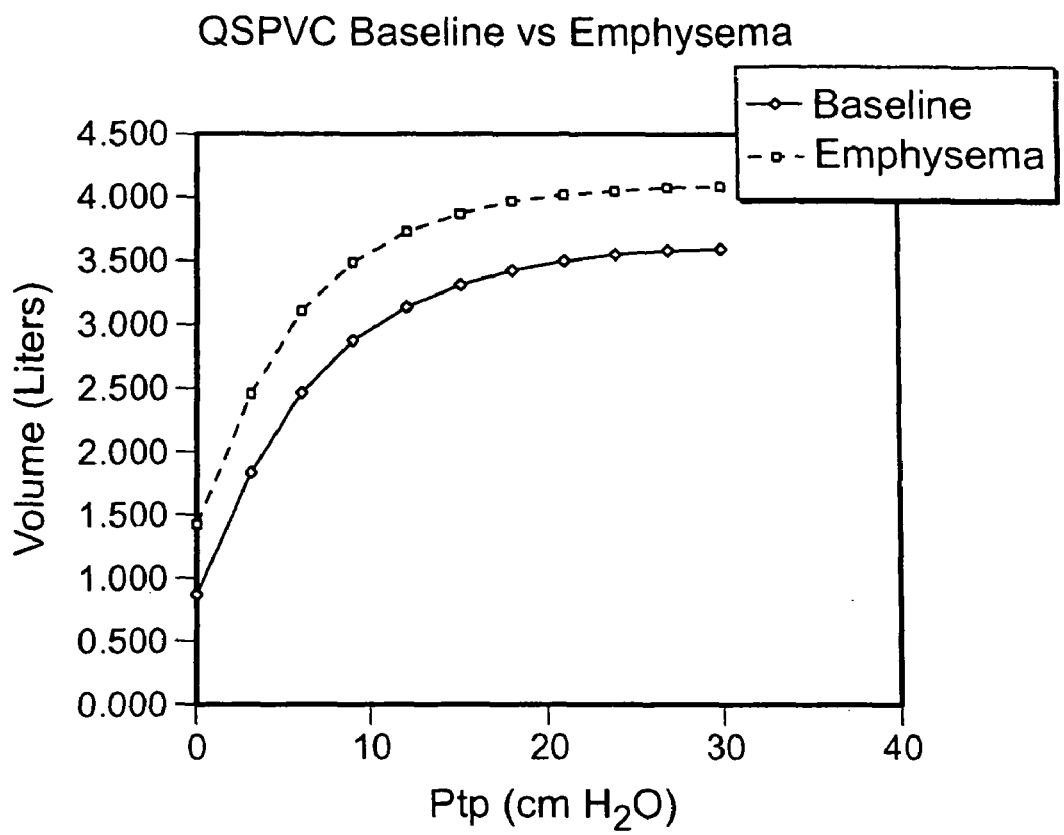
FIG. 7 is a line graph showing the relationship between lung volume (liters) and Ptp (cm $H_2O$) in untreated animals (solid line; baseline) and those treated with papain to model emphysema (dotted line; emphysema). There is a significant increase in lung volume (measured by plethysmography) in the papain-treated animals, which demonstrates hyperinflation as a result of tissue damage.
Figure 8:
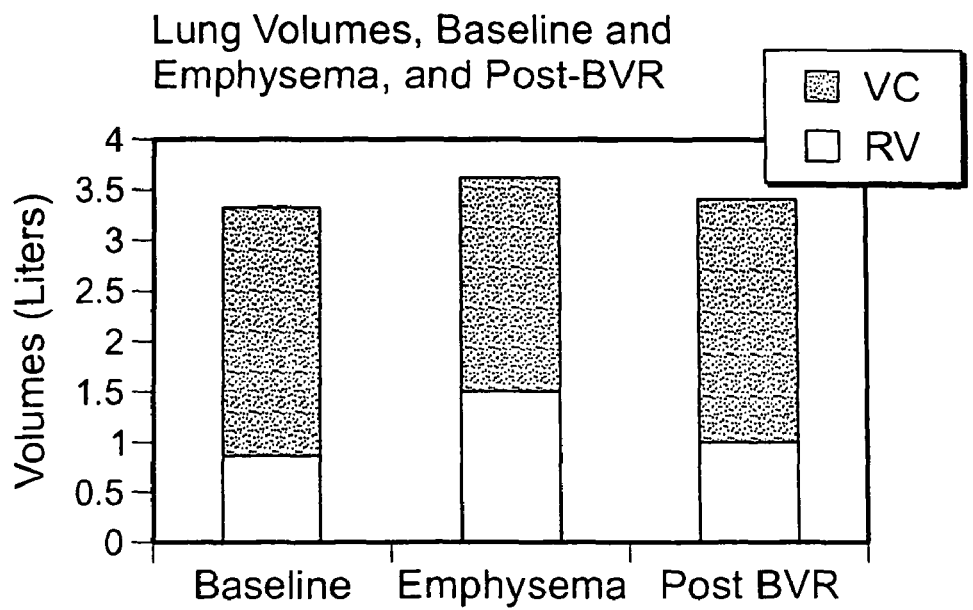
FIG. 8 is a bar graph showing lung volume (liters; VC=vital capacity, RV residual volume) in untreated animals (Baseline), papain-treated animals (Emphysema), and following treatment by enzyme pre-conditioning and BVR (Post BVR). These data demonstrate hyperinflation as a result of tissue damage, and a return to normal volumes after BVR.
Figure 9:
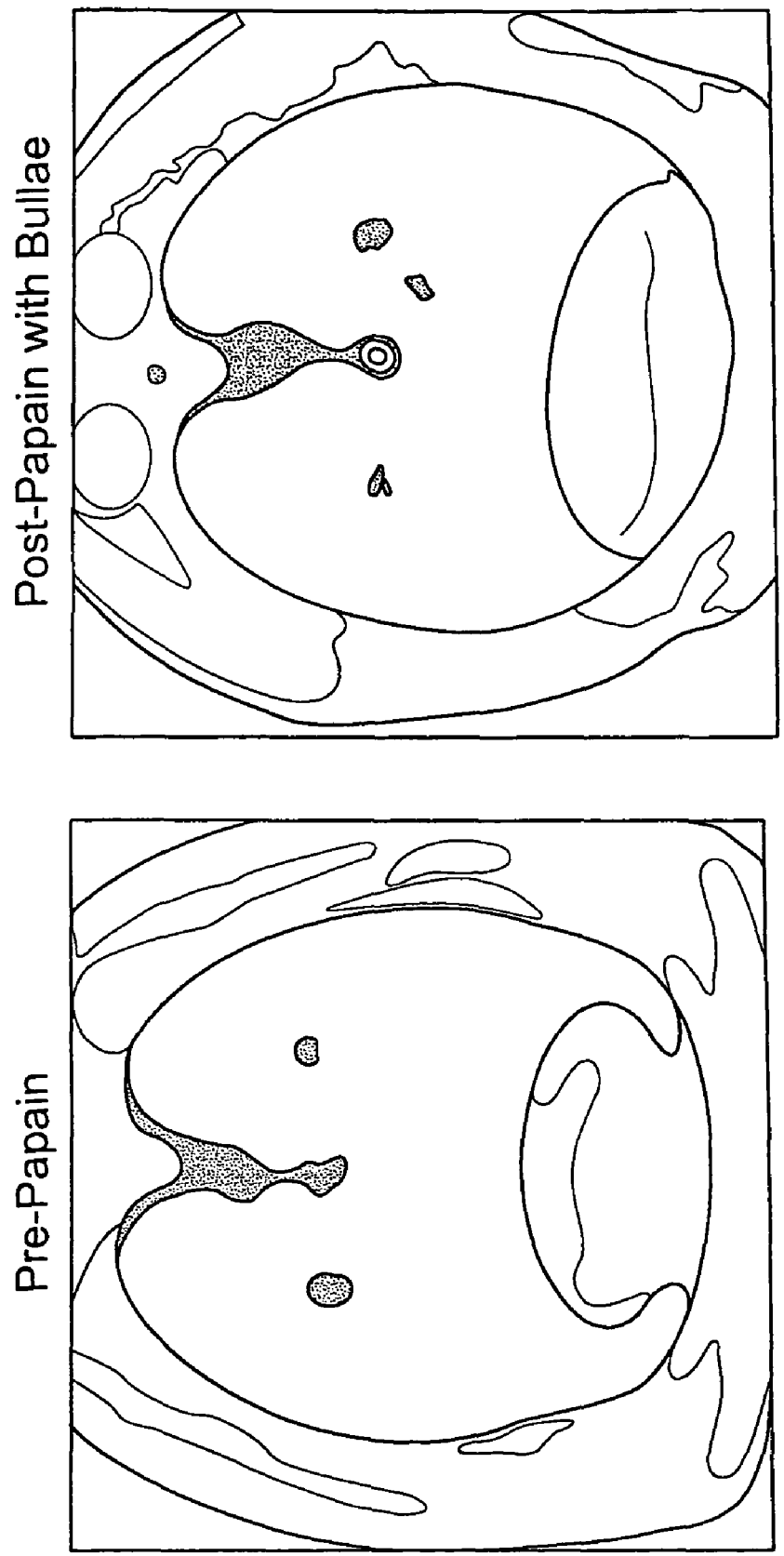
FIG. 9 is a pair of images of the chest cavity before treatment with papain (left-hand image) and after papain treatment (right-hand side). A cm bullous lesion is apparent after papain treatment.
Figure 11:
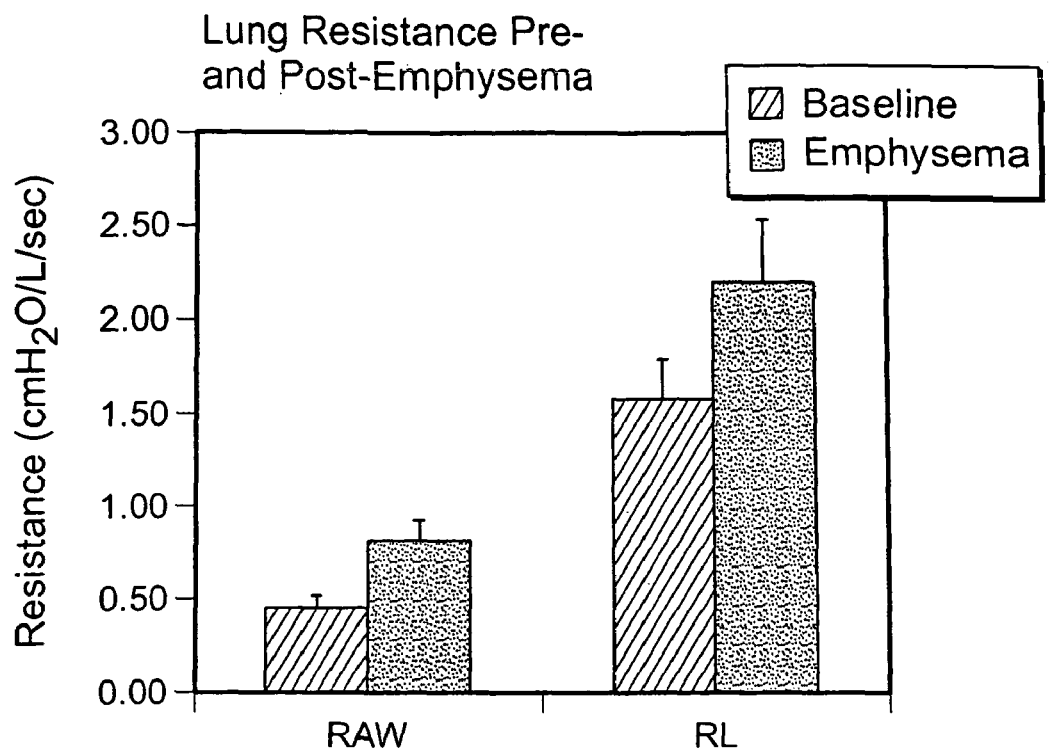
FIG. 11 is a bar graph illustrating lung resistance (cm $H_2O/L/sec$) before and after induction of emphysema by papain treatment. Compared to baseline (grey shading), post-papain-treated animals demonstrated an increase in total lung resistance of 40±9%, and an increase in airway resistance of 75±16%.
Figure 12:
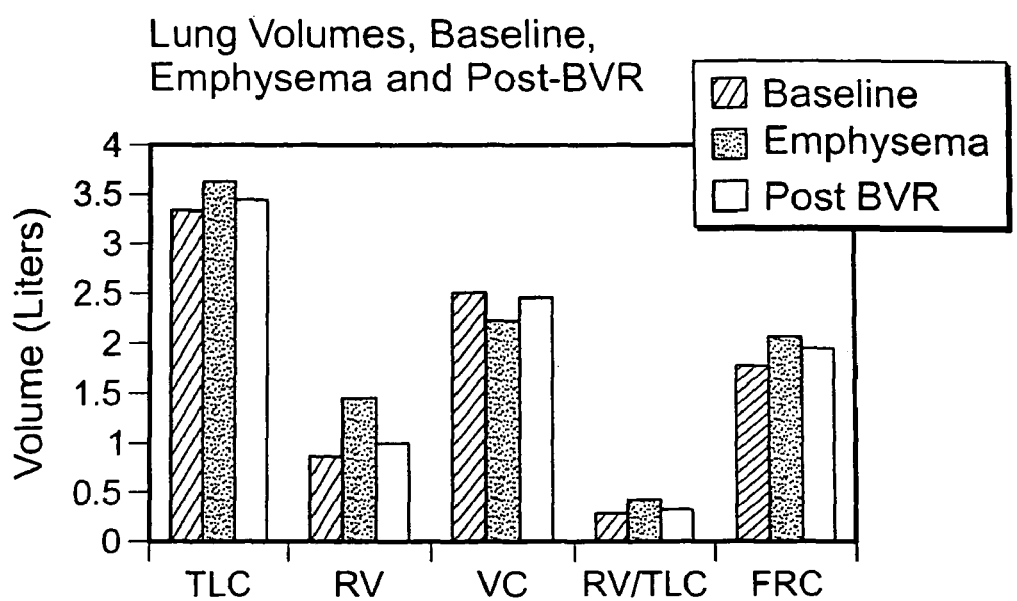
FIG. 12 is a bar graph illustrating lung volumes (in liters) in healthy animals (black bar; baseline) in animals treated with papain (grey bar; emphysema), and after enzyme pre-conditioning and BVR (white bar; Post BVR). Total lung capacity (TLC), the total volume within the lung, increased 10±3%, the residual volume (RV), the trapped gas within the lung, decreased 66±21%, and vital capacity (VC), the functional volume within the lung increased 11 ±4%.
Figure 13:
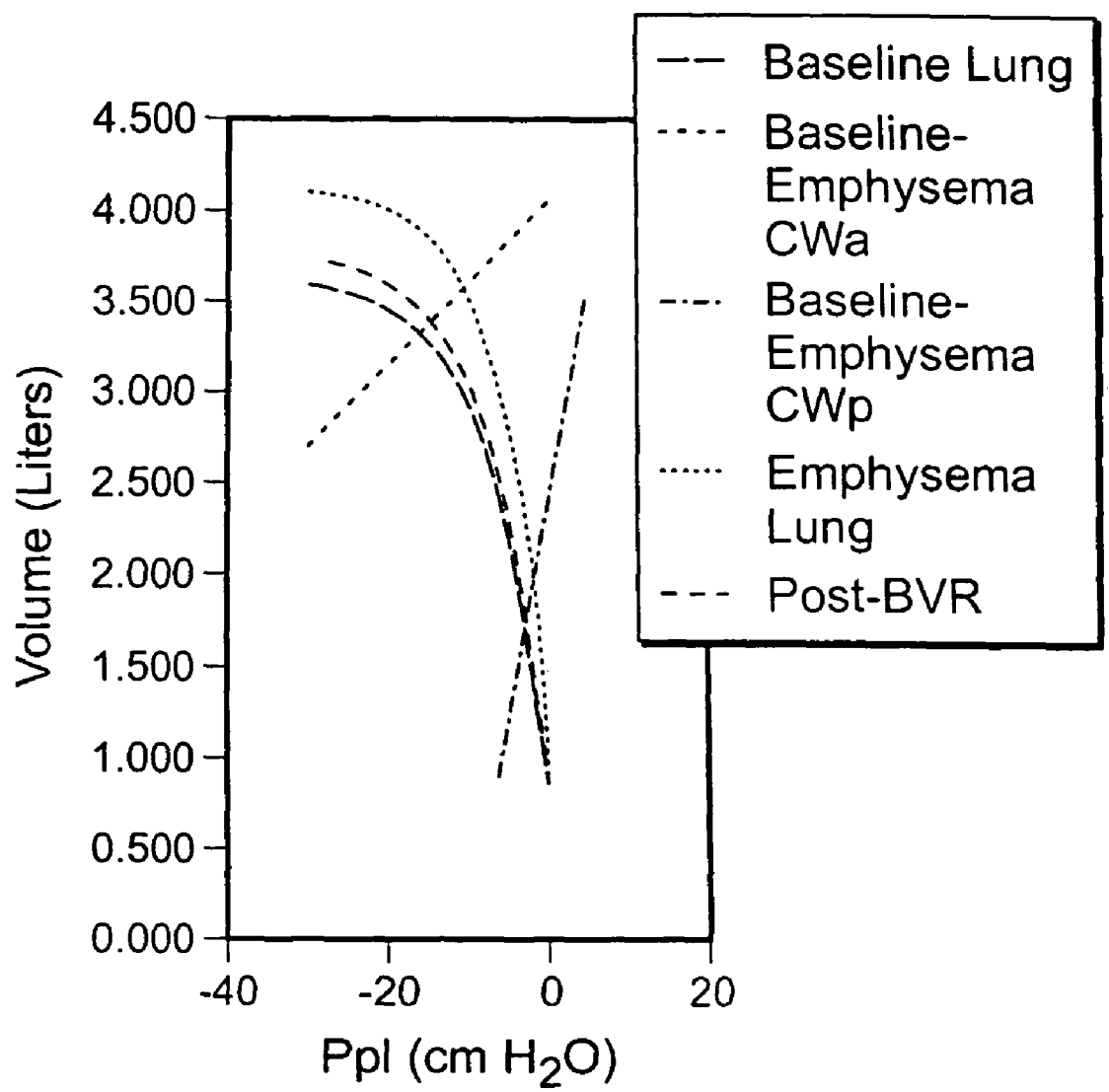
FIG. 13 is a Campbell diagram of baseline physiology, after induction of emphysema by papain treatment, and after enzyme pre-conditioning/BVR (see the legend; volume (liters) vs. Ppl (cm $H_2O$)). The diagram demonstrates the interrelationship between chest wall and lung mechanics that ultimately determines the static properties of the respiratory system. Papain-induced emphysema had no significant impact on either active (CWa) or passive (CWp) chest wall mechanics, but caused a significant increase in both total lung capacity (TLC) and RV.

The studies described below demonstrate that these preparations are among those effective in selectively ablating epithelial cells (the studies are performed in a large animal model of emphysema). Accordingly, the invention features methods in which proteases are used to disrupt epithelial cell attachment to the underlying sub-epithelial interstitium and basement membrane (FIGS. 6A and 6B), followed further by a therapeutic process (e.g., lung volume reduction (e.g., BLVR) or administration of a therapeutic agent to a cell that was previously at least partially obscured by an epithelial cell). The invention also features physiologically acceptable compositions that include one or more agents (e.g., proteases; see below) that disrupt the attachment between epithelial cells and surrounding or underlying cell types (e.g., subepithelial interstitium and/or basement membranes) for use as medicaments or for use in the preparation of medicaments for treating patients who have COPD (e.g., emphysema) or another disease or condition that would benefit from selective epithelial damage and subsequent fibrosis or scar formation (e.g., a disease or condition in which the target cells would otherwise be obscured by the epithelial lining of a tissue or one that can be treated with an implanted device (e.g., a stent or a valve, pump, or prosthetic device)).

A variety of different proteases, including serine proteases, can be used. Serine proteases are a superfamily of enzymes that catalyze the hydrolysis of covalent peptidic bonds. In the case of serine proteases, the mechanism is based on nucleophilic attack of the targeted peptidic bond by a serine. Cysteine, threonine or water molecules associated with aspartate or metals may also play this role. In many cases, the nucleophilic property of the group is improved by the presence of a histidine, held in a "proton acceptor state" by an aspartate. Aligned side chains of serine, histidine and aspartate build the catalytic triad common to most serine proteases.

There are approximately 700 serine proteases, grouped into 30 families, and further grouped into 5 clans. Representative members of these families, any of which can be used in the methods described herein (and any of which can be used for the manufacture of a medicament for use in treating a patient who has COPD (e.g., emphysema) or another condition which would benefit from controlled epithelial cell damage), include trypsin, chymotrypsin, alpha-lytic endopeptidase, alpha-lytic endopeptidase, glutamyl endopeptidase (V8), protease Do (htrA) (*Escherichia*), togavirin, lysyl endopeptidase, IgA-specific serine endopeptidase, flavivirin, hepatitis C virus NS3 endopeptidase, tobacco etch virus 35 Kd endopeptidase, cattle diarrhea virus p80 endopeptidase, equine arteritis virus putative endopeptidase, apple stem grooving virus serine endopeptidase, subtilases, subtilisin, kexin, tripeptidyl-peptidase II, prolyl oligopeptidase, prolyl oligopeptidase, dipeptidyl-peptidase IV, acylaminoacyl-peptidase, carboxypeptidase C, lactococcus X-Pro dipeptidyl-peptidase, lysosomal Pro-X carboxypeptidase, D-Ala-D-Ala peptidase family 1, D-Ala-D-Ala peptidase family 2, D-Ala-D-Ala peptidase family 3, ClpP endopeptidase, endopeptidase La (Lon), LexA repressor, bacterial leader peptidase I, eukaryote signal peptidase, omptin, coccidiodes endopeptidase, and assemblin (Herpesviruses protease). The invention also features physiologically acceptable compositions that include one or more of these enzymes for use as medicaments or for use in the preparation of medicaments for treating patients who have a disease or condition that would benefit from selective epithelial damage and subsequent fibrosis or scar formation (e.g., a disease or condition in which the target cells would otherwise be obscured by the epithelial lining of a tissue or one that can be treated with an implanted device (e.g., a stent or a valve, pump, or prosthetic device)).

Enzymatic preparations are described further below. We note here, however, that the concentration of the enzyme(s) within the preparation can be readily determined by one of ordinary skill in the art and will be such that the epithelial cell lining will be damaged (e.g., by loss of epithelial cells) but the cells (e.g. mesenchymal cells) under that lining will be substantially unaffected (in the lung, the underlying cells will not be so affected that they cannot mediate fibrosis). This can be determined by, for example, histological analysis or by assessing outcome (e.g., if there is no indication of fibrosis, the enzyme treatment may have destroyed the underlying fibroblasts, indicating that the concentration of the enzyme or the length of the treatment is excessive). Such determinations can be made in large animal models before human clinical trials.

When trypsin is included in the preparation, it can be present as 0.1-10.0% (w/v) of the solution (e.g., 0.1-9.0%, 0.1-8.0%, 0.1-7.0%, 0.1-6.0%, 0.1-5.0%, 0-14.0%, 0.1-3.0%, 0.1-2.0%, 0.1-1.0%, 0.2-0.8%, 0.2-0.5%, or about 0.1%, 0.2%, 0.5%, 0.8% or 1.0%, or about 5.0-10.0%, 6.0-10.0%, 7.0-10.0%, 8.0-10.0%, or 9.0-10.0%).

When collagenase (e.g., Type I collagenase, collagenase IV, or any other collagenase or combination thereof) is included in the preparation (e.g., as for any of the other compositions described herein, a physiologically acceptable composition useful for treating a patient who has COPD (e.g., emphysema) or in the manufacture of a medicament for use in treating such a patient), it can be present in the same percentage ranges given above for trypsin. Alternatively, one can include 50-100 U/ml of collagenase (e.g., 50-90, 50-80, 50-70, 50-60, 60-90, 70-90, 80-90, or 90-100 U/ml). When disspase is included in the preparation, it can be present in the same percentage ranges given above for trypsin. Alternatively, one can include 0.6-2.4 U/ml of disspase (e.g., 0.6-2.0, 0.6-1.8, 0.6-1.6, 0.6-1.4, 0.6-1.2, 0.6-1.0, 0.6-0.8, 0.8-1.0, 0.8-1.2, 1.0-2.0, 1.2-1.8, or 1.4-1.6 U/ml). When elastase is included in the preparation, it can be present in the same percentage ranges given above for trypsin. Alternatively, one can include 0.1-1.0 mg/ml elastase (e.g., 0.1-0.9, 0.2-0.8, 0.3-0.7, 0.4-0.6, about 0.5, 0.1-0.2, 0.1-0.3, 0.1-0.4, 0.1-0.5, 0.5-1.0 or 0.5-0.8 mg/ml). When chymotrypsin is included in the preparation, it can be present in the same percentage ranges given above for trypsin. Alternatively, one can include 0.1-1.0 mg/ml chymotrypsin (e.g., 0.1-0.9, 0.2-0.8, 0.3-0.7, 0.4-0.6, about 0.5, 0.1-0.2, 0.1-0.3, 0.1-0.4, 0.1-0.5, 0.5-1.0 or 0.5-0.8 mg/ml chymotrypsin).

The enzyme-containing preparation can be removed from the area if desired by, for example, suction or with an absorbent material. In the event the preparation is administered to a region within the lung, it can be applied through a catheter inserted through the working channel of a bronchoscope, and removed by subsequently inserting a suction tube through the catheter. To contain the solution (and this is true of any of the solutions described herein) within a particular region of the lung, one can use a balloon-tipped catheter (or other occluding device); when the balloon is inflated, it occludes the passageway to the distal portions of the lung.

An enzyme-containing preparation can also be affected by applying a neutralizing solution that inhibits the activity of the enzyme used (inhibition need not be complete in order for the neutralizing solution to be effective). A neutralizing solution can include a protein (e.g., an antibody) that specifically binds the enzyme and thereby inhibits its functional activity or it can include a nonspecific agent, such as serum and/or aprotinin.

Any of the enzyme-containing compositions described here can be formulated as physiologically acceptable compositions that can be used to treat, or used in the preparation of a medicament to treat, patients who have COPD (e.g., emphysema) or another disease or condition that would benefit from selective epithelial damage and subsequent fibrosis or scar formation (e.g., a disease or condition in which the target cells would otherwise be obscured by the epithelial lining of a tissue or one that can be treated with an implanted device (e.g., a stent or a valve, pump, or prosthetic device).

Methods that Employ Detergents In addition to, or as an alternative to, other methods described herein, tissue (e.g. lung tissue) can be exposed to a detergent. A detergent may be provided as a solution that can be administered using methods described herein. The amount and strength of a detergent that is administered to a subject can be optimized to permeabilize, damage, and/or disrupt epithelial cells in the area of the lung that is contacted by the detergent. The amount and strength of a detergent that is used can also be adjusted as a function of the duration of tissue exposure to the detergent. In some embodiments, a detergent may permeabilize, damage, and/or disrupt epithelial cells in a target tissue area without significantly damaging the basement membrane or other surrounding tissue.

Detergents include compounds with both a hydrophilic portion and a hydrophobic portion. Detergents can be ionic or non-ionic. Non-ionic detergents are generally preferred, because they are generally less toxic than ionic detergents. In addition, non-ionic detergents are generally more effective for cell lysis. However, any type of detergent can be used for the invention. Preferably, the detergent is either i) non-toxic or ii) used in an amount and/or for a time that is non-toxic. Preferably, the detergent is either i) effective for permeabilizing or disrupting a cell membrane and/or for cell lysis or ii) used in an amount and/or for a time that is effective for permeabilizing or disrupting a cell membrane and/or for cell lysis.

Ionic detergents can be anionic, zwitterionic, or cationic. Anionic detergents have a negatively charged hydrophilic portion that can be a carboxylate, a sulfate, a sulfonate, an other negatively charged moiety, or a combination thereof. Such detergents are typically in the form of a salt such as an alkali metal salt (e.g. $Na^+$ or $K^+$). Anionic detergents include SDS. Cationic detergents have a positively charged hydrophilic portion. Typical cationic detergents include quaternary ammonium compounds. Such compounds are often in the form of a halide salt. Cationic detergents include cetyl trimethylammonium bromide (CTAB). Zwitterionic detergents have a hydrophilic portion that includes both negatively and positively charged moieties. However, typical zwitterionic detergents are neutral. Nonetheless, some zwitterionic detergents are polarized. Examples of zwitterionic detergents moieties include betaines and sulfobetaines. Zwitterionic detergents include CAPS.

Non-ionic detergents have a non-charged hydrophilic portion. Typical non-ionic detergents include one or more hydroxyl groups. Examples of non-ionic hydrophilic portions include polyoxyethylenes and/or saccharides.

Detergents with any one or more types of hydrophobic portion can be used in the invention. Preferred hydrophobic portions include straight- or branched-chain hydrocarbon moieties and/or steroidal moieties. Detergents can include any one or more hydrophilic and any one or more hydrophobic portions described herein.

In one embodiment, non-ionic detergents include non-ionic sorbital-based detergents. These are frequently used in experimental studies to cause cell disruption and allow access to intracellular organelles, proteins, and nucleic acids. These agents are amphipathic (i.e. are both water and lipid soluble) and work by integrating into the cell membrane, causing dissolution of the membrane barrier and release of the cytoplasm into the extracellular environment. Examples of such non-ionic detergents include polyoxyethelenesorbitan monolaurate, polyoxyethelenesorbitan monopalmitate, polyoxyethelenesorbitan monostearate, and polyoxyethelenesorbitan tristearate.

In one embodiment, for the purpose of promoting airway and alveolar collapse, both of which may be desirable for achieving non-surgical lung volume reduction, a detergent can also act to inhibit natural lung surfactant.

Detergent solutions can include one or more of the detergents described herein. In particular, detergent solutions can include one or more the following: a polyoxyethelenesorbitan lipid mixture, a monolaurate, a monopalmitate, and a monostearate.

In some embodiments, detergents may be stable at room temperature, can be delivered as aqueous solutions through a catheter into the lung, and can be washed out from the treatment areas using aqueous solution. The exact duration of exposure may vary depending upon the specific application, but effective cell disruption may be complete within minutes. Exposure times can range from about 1 minute to about 1 hour. However, longer or shorter times can be used. Preferred exposure durations are between about 30 seconds and 30 minutes. Preferred exposure durations can be about 1, 2, 3, 4, 5, 6, 7, 8, 9, 10, 15, 20, 25, or 30 minutes long. The duration of the exposure is determined by the time between the administration of the detergent and the subsequent wash step using a solution to remove (or otherwise neutralize) the detergent or substantially all of the detergent.

It should be appreciated that the concentration of detergent to be used can be optimized experimentally. However, the duration of exposure and the type of detergent (e.g. it's ability to disrupt cell membranes) are important considerations. In one aspect, an appropriate detergent concentration may be chosen as one that results in 50% to 90% lysis (preferably about 80% lysis) in the following in vitro assay. A flask of cells (e.g. fibroblast 3T3 cells, epithelial A549 cells or other cells including other epithelial or fibroblast cell lines) is trypsinized and the cell suspension is split 1/10 and grown to about 80% confluence in a flask. A detergent solution is added to this flask and left for about 2 minutes before being washed out. The detergent may be provided in an isotonic salt solution. The volume of detergent used depends on the size of the flask (for example, about 1 ml of detergent solution is used for a T25 flask and about 5 mls of detergent solution are used for a T75 flask). After the detergent is washed out (e.g. using an isotonic solution) the percentage of lysed cells is evaluated. The cells may be stained using Trypan or another stain. The percentage of lysed cells may be calculated by comparing pictures of the flask surface (on which the cells were grown)

before and after detergent exposure. The percentage lysis can be approximated by calculating the percentage of the flask surface that was cleared by the detergent. By testing different detergent concentrations, a concentration that produces the desired degree of lysis can be identified. In one embodiment, a detergent solution at the chosen concentration may be administered therapeutically to a patient's lung for about 2 minutes before being washed out. In one embodiment, about 10 mls of detergent solution may be delivered to a target region. For many detergents, a range of concentration may be effective. For example, in certain embodiments, between 0.25% and 2% Tween 40 may be used. However, other concentrations also may be used (e.g. 0.1% to 5.0%). Higher or lower concentrations may be used depending on the potency of the detergent and the time of exposure to the tissue. For example, a lower concentration may be used when a more potent detergent is used or when a longer exposure time is used. Certain detergents may be more potent when they have a higher molecular weight and/or a higher number of acyl side chains. For example, Tween 80 is more potent than Tween 40.

Wash solutions include aqueous solutions, and may be buffered at physiological pH. Wash solutions may include salt solutions such as NaCl solutions. Wash solutions may be iso-osmotic with the tissue or cells being contacted. Wash solutions may include one or more components that solubilize the detergent in order to help remove it from the lung. Accordingly, wash solution components can include one or more lipids such as phospholipids (e.g. phophatidyl choline (PPC)). Wash solution components can also include one or more alcohols such as ethanol. In one embodiment, ethanol may be used in an aqueous solution at a concentration of between about 0.1 and about 5% ethanol to limit any undesirable effects of ethanol. Other alcohols can be used at similar concentrations, lower concentrations, or higher concentrations.

In one embodiment, about 10 mls of a detergent solution may be used for a target lung region. Similarly, about 10 mls of a wash solution may be used. However, smaller or larger volumes may be used. A 10 ml volume contacts approximately 2-3% (approximately 600,000 alveoli) of the lung.

Localization of reagent to the intended treatment site can be achieved by injecting the material through an inflatable balloon catheter that prevents leakage of material back into the airways, or by injecting the material through the channel of the bronchoscope, and maintaining the scope in the wedge position (positioning it so it fits tightly against the walls of the airways) during adminstration. Other occluding devices also may be used following exposure, residual materials can be suctioned from the site of treatment.

In one aspect, methods of the invention can be used to target one or more regions of the lung by contacting one or more regions with a detergent volume and subsequently removing the detergent and washing the one or more regions as discussed above. If several regions are targeted, it may be desirable to use approximately 10 mls of solution for each region as discussed herein. However, smaller or lager volumes can also be used (e.g. from about 1 mls to about 10 mls, or from about 10 mls to about 50 mls, or less than 1 ml or more than 50 mls).

In one embodiment, a detergent may be included in an adhesive composition in order to promote fibrosis in the lung. However, it should be appreciated that a lower concentration of detergent (or a detergent with lower potency) may be desirable in order to minimize any long term damage to the tissue lining the lung.

Methods that Employ Polycations

In one aspect of the invention, one or more polycations may be included in an adhesive composition, and used for lung volume reduction without using a cell-disrupting primer composition (e.g. without using a trypsin primer solution). In one embodiment, the presence of one or more polycations in an adhesive composition is sufficient to promote fibrosis and scarring. However, in other embodiments, a polycation primer solution also may be used instead of a primer solution containing an enzyme (e.g. trypsin) or a detergent. According to aspects of the invention, a variety of polycations may be used, including but not limited to poly-L-lysine (PLL), poly-L-arginine, poly-ornithine, and poly-ethylamine. A variety of concentrations may be used (e.g. from 0.1% to 5.0%, or about 0.5%, or about 1%, or about 2%). Higher or lower concentrations also may be used depending on the potency of the polycation and whether or not a primer solution is used. It should be appreciated that different polycations may have different potencies. For example, the following polycations are listed in decreasing order of potency: poly-ethylamine, poly-L-lysine, poly-arginine, and poly-ornithine.

In one aspect of the invention, the potency of a polycation may be evaluated by growing cells on hydrogels (e.g. split a cell suspension ¹⁄₁₀ and lay it on a 3% fibrinogen gel) that include different concentrations of one or more polycations. In one embodiment, the cells are then incubated for about 72 hours. At low concentrations, a polycation may facilitate cell attachment. However, at higher concentrations, a polycation may be toxic and cause cells to round up and die. According to one aspect of the invention, polycation concentrations that are toxic and prevent cell growth or cause cells to die are chosen to include in a composition (e.g. a primer composition and/or an adhesive composition) for lung volume reduction. In general, higher MW polycations are more toxic. For example, a composition may contain PLL with a MW of between 75 and 150 kD. However, other molecular weights may be used. PLL may be toxic at 0.1%, 1% and higher concentrations in adhesive solutions. Accordingly, in one embodiment, an adhesive solution with 0.1%, 1%, or more PLL (or other polycation), may be used for lung volume reduction without using an enzyme or detergent pre-treatment. In one embodiment, an adhesive solution also may contain 0.1%, 1%, or more, CS. CS may act as a scaffold for fibrosis by acting as an anchor for collagen and/or fibroblasts.

Methods that Employ Mechanical Force

Figure 1B:
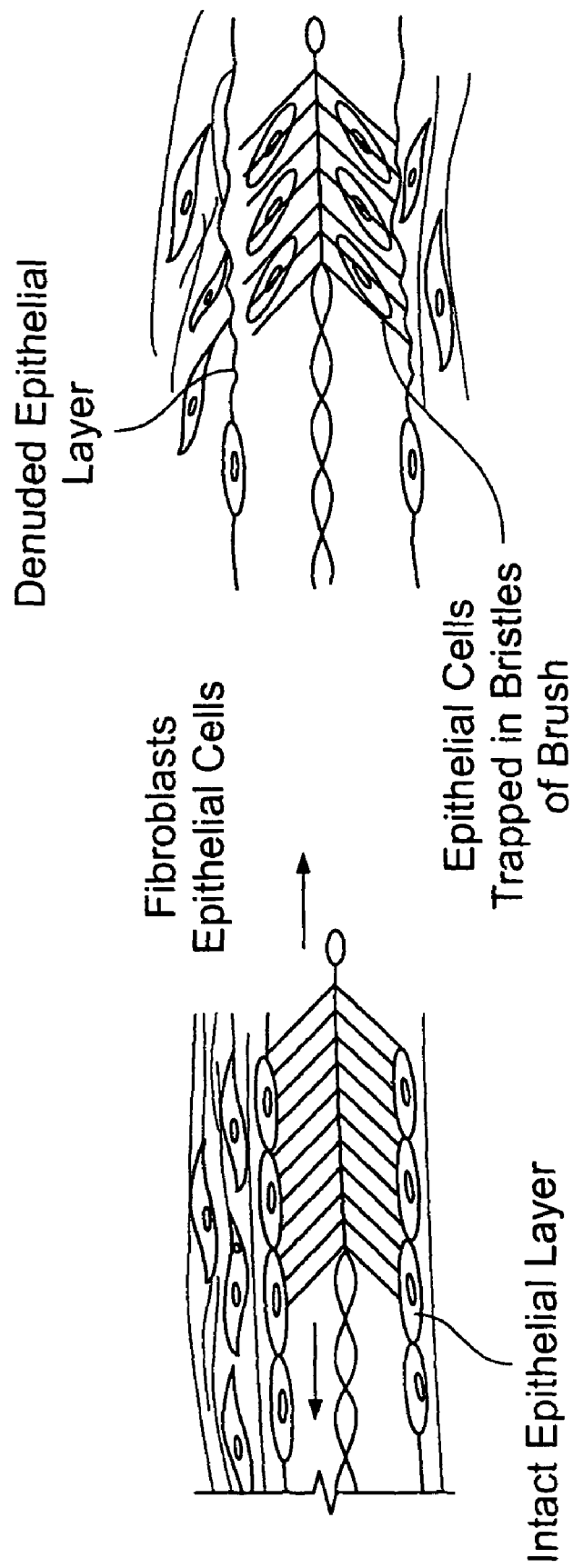

In addition to, or as an alternative to, the chemical (e.g., enzymatic) treatments described herein, tissue (e.g., lung tissue) can be exposed to a mechanical force that damages the epithelium. For example, one can simply brush or otherwise abrade the selected region with, for example, a cytology brush specifically designed for the organ in question. For example, the brush can include short bristles that are capable of de-epithelializing a particular region of the airway in preparation for non-surgical (e.g., bronchoscopic) volume reduction therapy (FIG. 1). This embodiment can include the use of a small (1.5-2.0 mm) brush that can be passed into multiple small airways of the projected target region and gently rubbed to remove the selected cells (brushes having an outer diameter of 2-5 mm can be obtained from Bard Endoscopy and U.S. Endoscopy; other commercial suppliers and other brushes are readily available).

If desired, the epithelial cells that have been removed (i.e., ablated) from the target region can be washed away by administering a physiologically compatible solution (e.g., saline or a buffered solution such as phosphate-buffered saline). The "rinsing agent" can be applied through a catheter or tube inserted through a working channel of the bronchoscope and removed by applying suction to the same or a different device inserted into the target region (more generally, and regardless of the manner in which epithelial cells are ablated, those cells can be removed from the target region before a therapeutic procedure is carried out or a therapeutic agent is administered). An anti-surfactant (e.g. fibrin or fibrinogen, a detergent, another biological, or synthetic hydrogel, etc. that increases the surface tension in a patient's lung), suction, or a mechanical blockade (e.g., using a stent or a valve or other occluding device) of the airway can then be applied to induce regional collapse (the collapsed region containing at least some portions in which the epithelial lining was damaged). As following other methods of inducing epithelial damage and regional collapse, a reagent such as a fibrin-based hydrogel can be applied to promote scar formation and improve the strength or duration of the collapse.

Methods that Employ Ultrasonic Energy

Figure 2A:
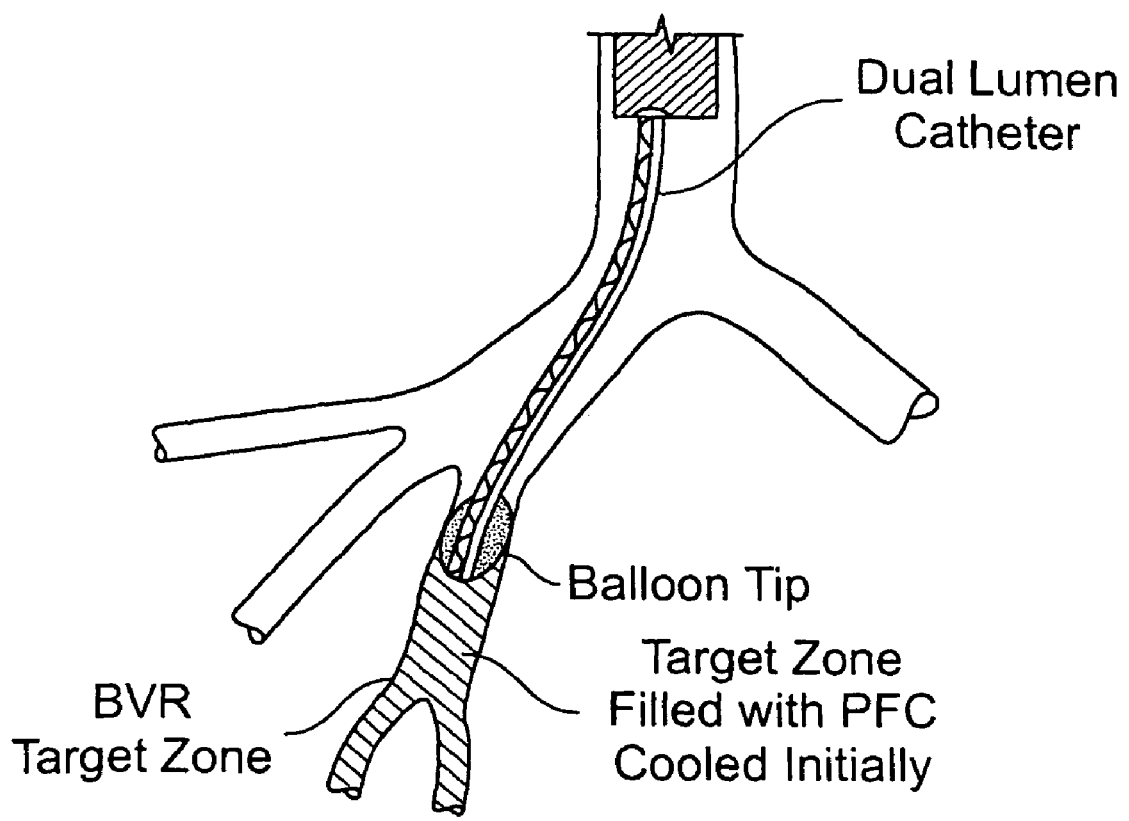
FIGS. 2A and 2B are schematic representations of a method for damaging epithelial cells within the lung using ultrasonic energy.
Figure 2B:
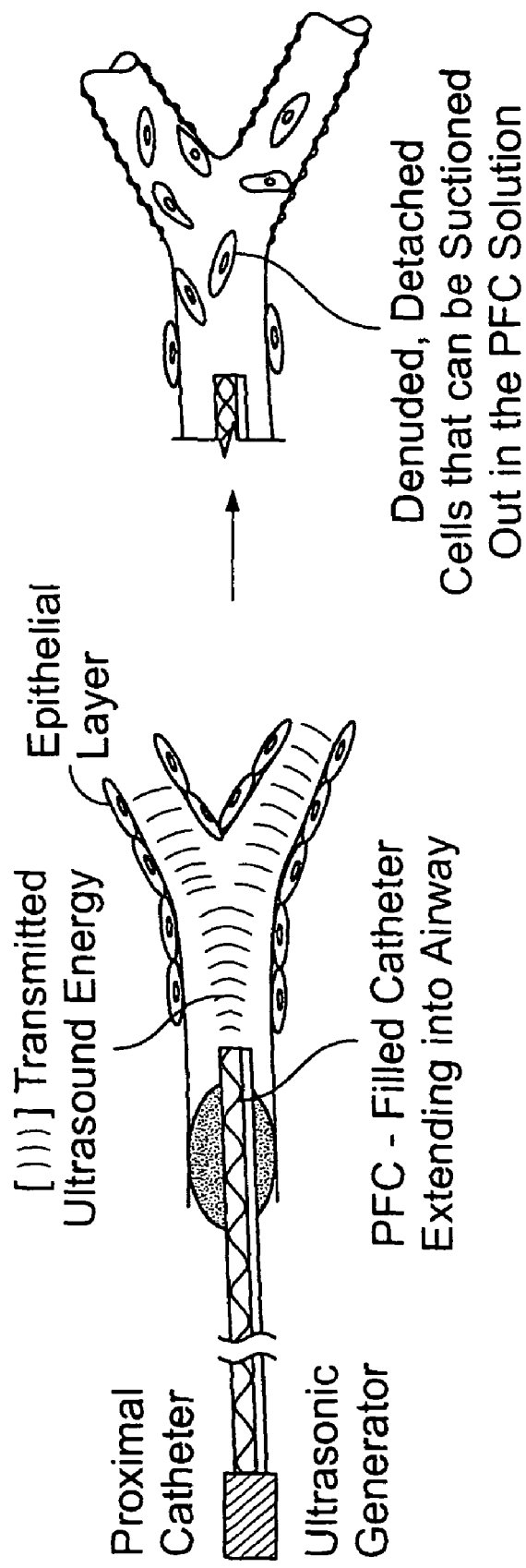

In addition to, or as an alternative to, enzymatic treatment, tissue (e.g., lung tissue) can be exposed to ultrasonic energy that damages the epithelium. Sonication is a biophysical technique that is frequently used in cell and molecular biology to disrupt cell membranes (see, e.g., Hunter and Hanrath, *Thorax* 47:565, 1992). In the context of the present invention, focused ultrasonic energy may be applied selectively to the epithelial surface to damage (e.g., remove cells from) the epithelial layer. The specific target organ or a region thereof (e.g., all or part of an over-inflated region of the lung) can be filled with (or can include) a liquid carrier reagent that is excited with an ultrasonic probe (the ultrasonic source being at a proximal location). The carrier reagent can be a high-density perfluorocarbon, which facilitates oxygen and carbon dioxide transport and readily transmits ultrasonic energy (FIGS. 2A and 2B). The carrier reagent, and any epithelial cells contained within it, can be removed (by, for example, suction). If desired, the affected region can also be rinsed with a physiologically compatible solution (e.g., saline or a buffered solution such as phosphate-buffered saline). The "rinsing agent" can be applied through a catheter or tube inserted through a working channel of the bronchoscope and removed by applying suction to the same or a different device inserted into the target region. As following other methods of inducing epithelial damage, an anti-surfactant (e.g. fibrin), suction, or a mechanical blockade of the airway can then be applied to induce regional collapse (the collapsed region containing at least some portions in which the epithelial lining was damaged). As following other methods of inducing epithelial damage and regional collapse, a reagent such as a fibrin-based hydrogel (or other hydrogel) can be applied to promote adhesion and/or scar formation and improve the strength or duration of the collapse.

Methods that Employ Thermal Energy

Figure 3A:
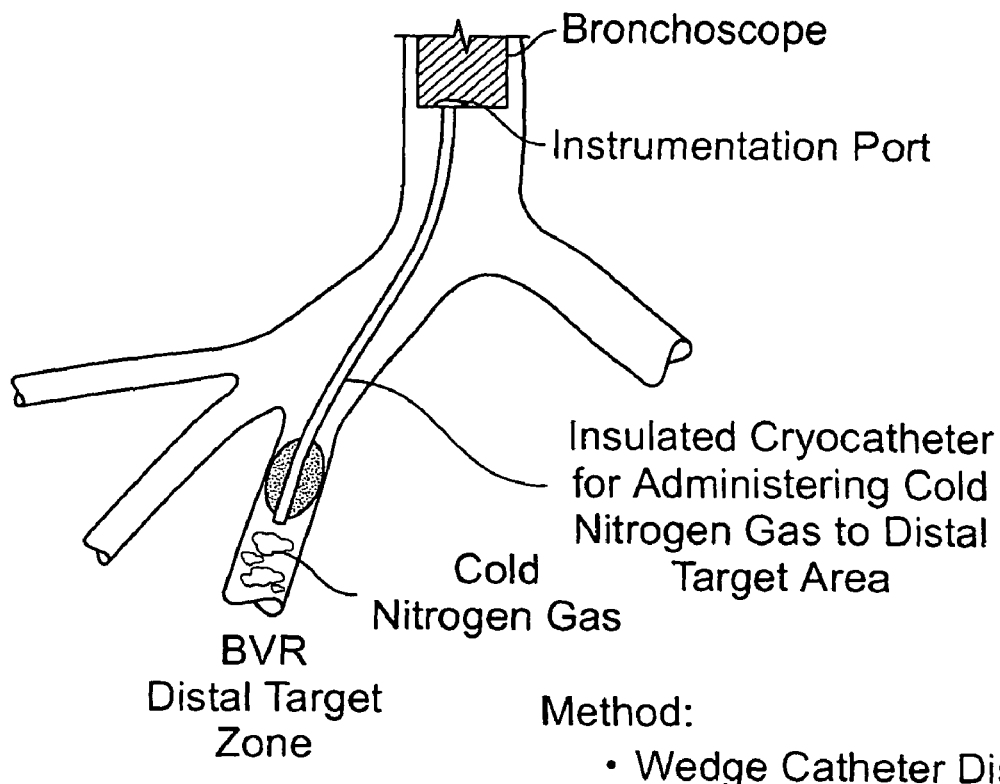
FIGS. 3A and 3B are schematic representations of a method for damaging epithelial cells within the lung using thermal energy.
Figure 3B:
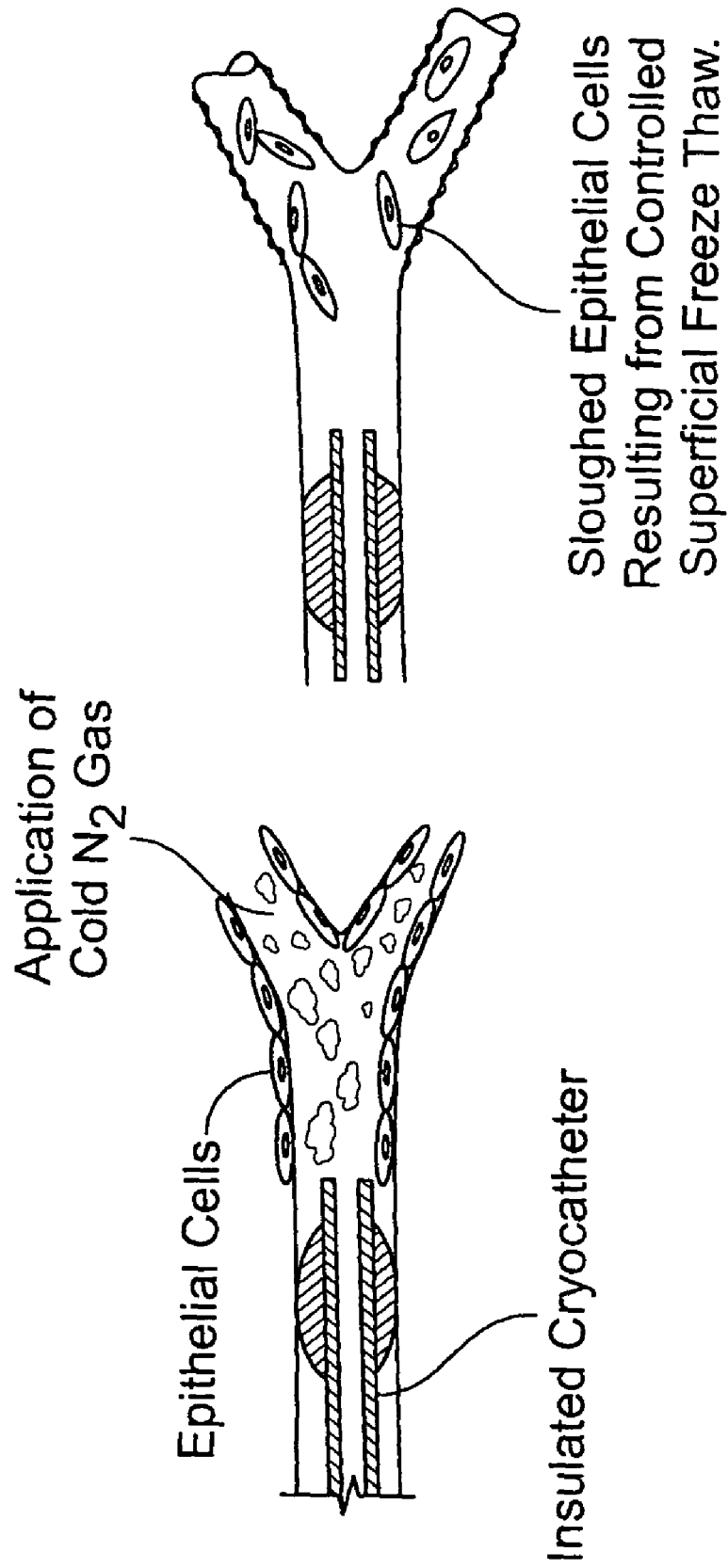

In addition to, or as an alternative to, other methods for damaging the epithelium, tissue (e.g., lung tissue) can be exposed to thermal energy (heat or cold) that damages the epithelium (see FIGS. 3A and 3B). For example, both heat, applied as laser energy, and cold applied via a cryoprobe have proven effective in "necrosing" endobronchial lesions, primarily cancers. Cryoprobes that are identical to or similar to those currently used could be applied to cause superficial damage to target regions of lung (see, e.g., Angel, *Cryotherapy and electrocautery in the management of airway tumors*, presented in: Multimodality management of tumors of the aerodigestive tract. Boston, Mass., November 2-3). Epithelial cells are more susceptible to damage by freeze-thaw cycles; than are interstitial cells. If desired, the affected region can be rinsed with a physiologically compatible solution, as described above, to remove epithelial cells that have become dislodged, and an anti-surfactant (e.g fibrin), suction, or a mechanical blockade of the airway can then be applied to induce regional collapse (the collapsed region containing at least some portions in which the epithelial lining was damaged). As following other methods of inducing epithelial damage and regional collapse, a reagent such as a fibrin-based hydrogel (or other hydrogel) can be applied to promote adhesion and/or scar formation and improve the strength or duration of the collapse.

Methods that Employ Electric Energy

In addition to, or as an alternative to, other methods for damaging the epithelium, tissue (e.g., lung tissue) can be exposed to an electric current using pre-selected energy levels and waveform patterns. The energy can be delivered to a selected region of the lung in a manner that causes epithelial cells to dislodge from the underlying basement membrane. Preferably, the current is applied so that adjacent issues are not significantly injured (see Angel, supra). To modulate (e.g., increase the effectiveness of) current delivery within target areas of lung, an electrolyte solution may be administered to those areas. This solution will wash out at least some of the naturally occurring surfactant within the lung, which contains lipids that limit energy transmission by acting as an insulator. The solution also acts as a chemical conduction system to further improve energy delivery. The solution can be administered and withdrawn (by, for example, suction) before the electrical current is applied; the residual layer serves as a sufficient conducting medium and improves energy transmission distal to the proximal current source.

The precise pattern of energy delivery may vary, depending upon whether proximal or distal de-epithelialization is desired. One of ordinary skill in the art would be able to determine the optimal pattern of energy to use to dislodge cells without causing significant injury. Programmable analog waveform, generators, or computerized digital wave generators may be used to deliver any of a variety of different patterns.

Figure 4A:
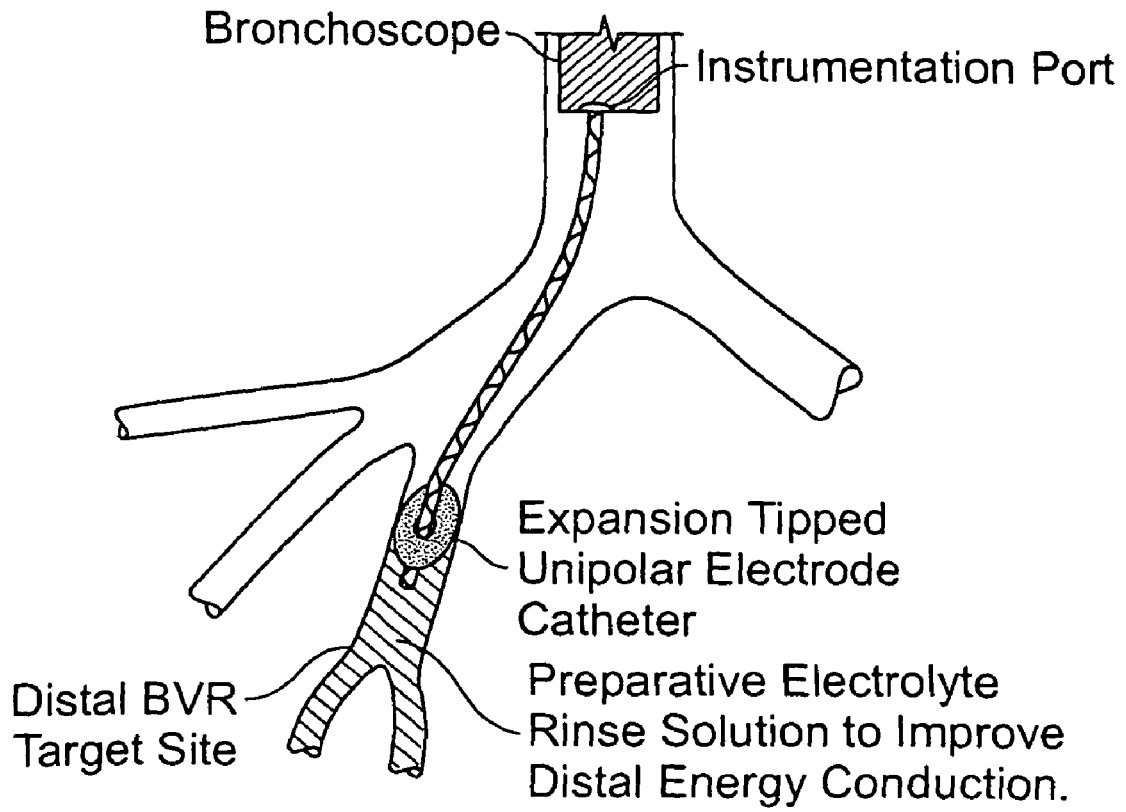
FIGS. 4A and 4B are schematic representations of a method for damaging epithelial cells within the lung using electrical energy.
Figure 4B:
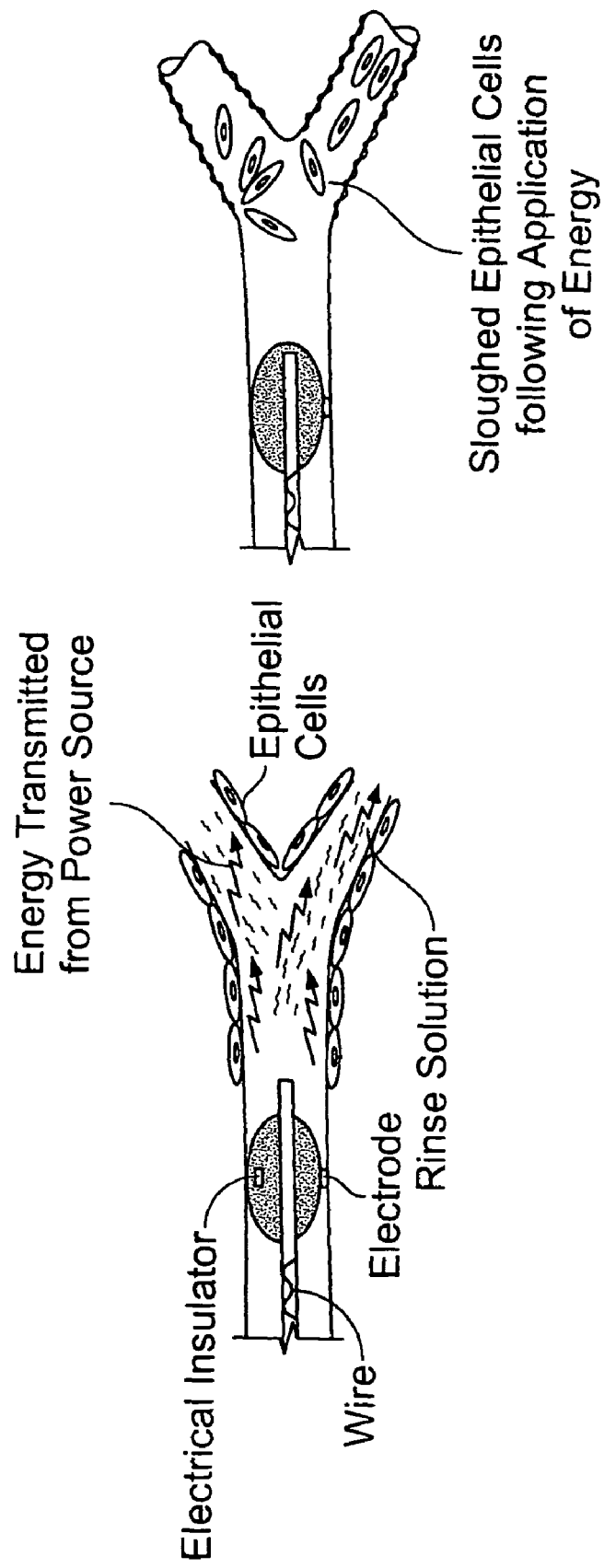

A unipolar catheter electrode may be used to transmit energy from the programmable energy source outside the patient distally into the lung. The electrode should be designed such that it is thin and flexible enough to fit through the channel of a fiber optic bronchoscope (FIGS. 4A and 4B). The purpose of the system is to transmit energy along the airway surface. Thus the conducting superficial electrode is circumferetially located, and positioned at the tip of the catheter to allow for insertion distally into the patient.

As following other methods of inducing epithelial damage, an anti-surfactant (e.g. fibrin), suction, or a mechanical blockade of the airway can be applied after the electric current to induce regional collapse (the collapsed region containing at least some portions in which the epithelial lining was damaged). As following other methods of inducing epithelial damage and regional collapse, a reagent such as a fibrin-based hydrogel (or other hydrogel) can be applied to promote adhesion and/or scar formation and improve the strength or duration of the collapse.

Methods that Employ Photo-Sensitizing Agents

In addition to, or as an alternative to, other methods for damaging the epithelium, tissue (e.g., lung tissue) photodynamic therapy (PDT) can be used to selectively ablate epithelial cells. PDT has proven clinically effective in generating targeted endobronchial tissue death (Pass, *J. Natl. Cancer Inst.* 85:443, 1993). This approach uses systemic therapy with a photosensitizing agent known as photophrin, a compound that is readily taken up by cells and renders them sensitive to light energy at a specific wavelength. The fluorescent properties of this intracellular dye result in tissue damage at sites wherever the monochromatic sensitizing light source is directed. As a result, site-specific endobronchial tissue injury can be generated. Accordingly, the invention features use of photodynamic or photo-sensitive agents (e.g., photophryin) for the manufacture of a medicament for use in treating a patient who has COPD (e.g., emphysema)

At present, PDT utilizes systemic photophrin exposure; site specificity is accomplished by carefully directed light application, and the present invention includes photodynamic preconditioning methods wherein the photophrin has been administered systemically. However, the invention also features methods in which a photo-sensitive agent (e.g., photofrin) is administered to the lung by way of a bronchoscope. Such localized application has advantages in that the patient is not required to remain in the dark for any period of time; with systemic administration, patients must avoid exposure to light until the photophrin is no longer present in active amounts. Localized administration (e.g., administration under bronchoscopic guidance) thus allows for greater control of photosensitivity. Optionally, the photo-sensitive agent can be mixed with or encapsulated within liposomes by methods known in the art prior to administration to a patient. The liposomal mixture may facilitate endobronchial spreading. Without limiting the invention to methods achieved by any particular cellular mechanism, the liposomal particles may be taken up by endocytosis into epithelial cells by the same pathway that is involved in surfactant recycling. Thus, the present invention also relates to photodynamic preconditioning methods wherein the photophrin has been administered selectively via liposomal delivery, and to the use of liposome-associated photodynamic or photo-sensitive agents for the manufacture of a medicament for use in treating a patient who has COPD (e.g, emphysema). As noted in connection with other epithelial cell damaging-agents described above, these compositions are also useful in treating patients (or in the preparation of a medicament for treating patients) who have suffered a traumatic injury; patients whose target cells are obscured from therapeutic agents by overlying epithelial cells; or patients who require an implantable device.

Figure 5A:
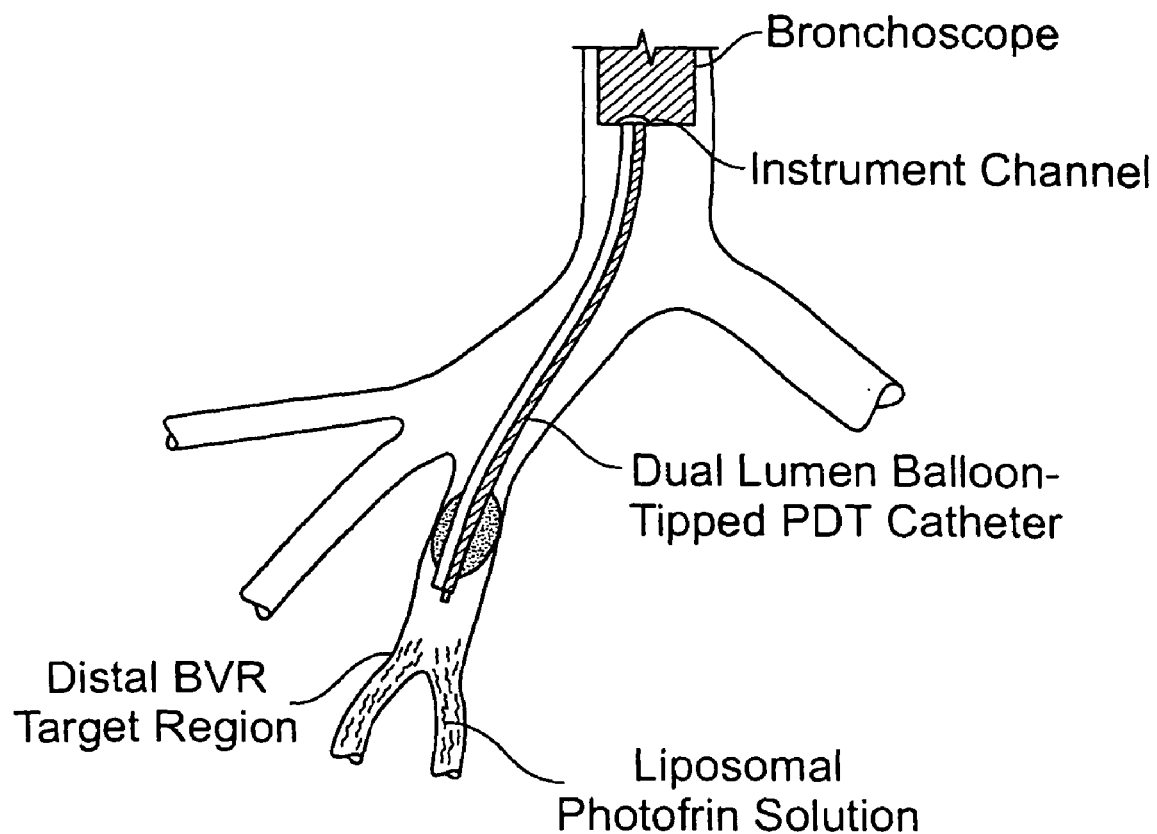
FIGS. 5A and 5B are schematic representations of a method for damaging epithelial cells within the lung using a photodynamic therapy (PDT).
Figure 5B:
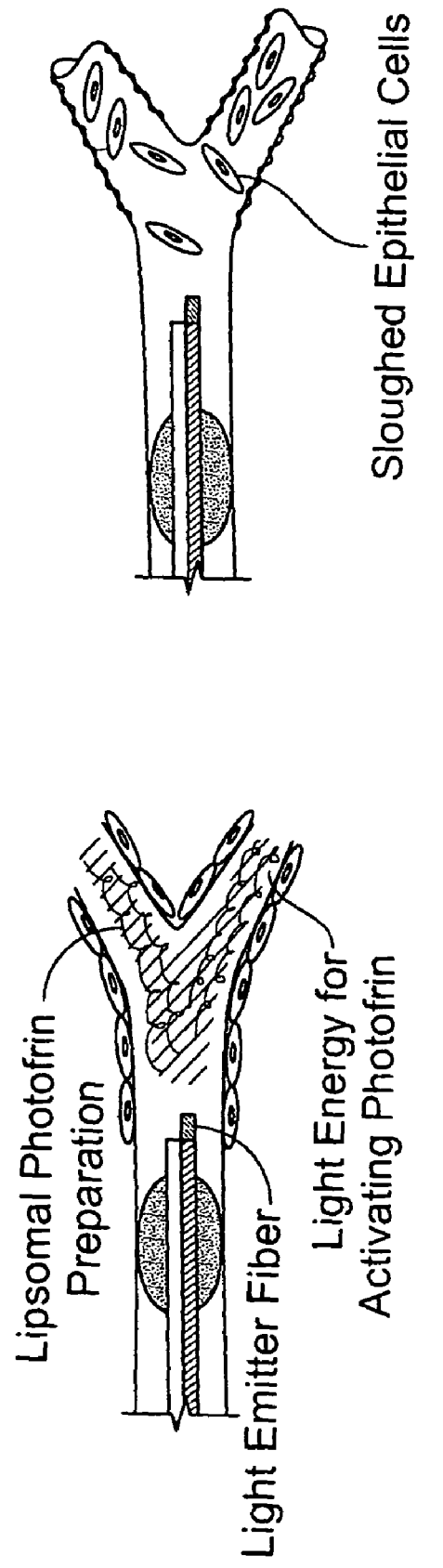

Regardless of the method of delivery, a specialized fiber optic PDT catheter and light wand may be used to administer energy at selected sites. For the purpose of BVR, epithelial "stripping" is necessary at the most distal sites, and thus the catheter system (see FIGS. 5A and 5B) would be designed specifically to ensure application of appropriate light energy at a very distal site. The liposomal photophrin compositions of the present invention may include the phospholipid dipalmitoylphosphatidylcholine (DPPC), a key lipid component of surfactant, which is readily taken up by epithelial cells. Light intensity, wavelength, and generation are selected based on studies conducted to ensure penetration of cytotoxic effect to a level that affects epithelial cells without causing more extensive damage. In a preferred embodiment, an anti-surfactant, suction or mechanical blockage of the airway is then applied to induce regional collapse. As described above, the induction of regional collapse is followed by injection of a reagent (e.g., a fibrin-based hydrogel) to promote adhesion and/or scar formation and help secure the area of collapse. Those of ordinary skill in the art may refer to one of the following publications for additional guidance in performing PDT: Kreimer-Bimbaum, *Seminars in Hematology* 2612:157-173, 1989; Koenig et al., "PDT of Tumor-Bearing Mice Using Liposome Delivered Texaphyrins," International Conference, Milan, Italy, Biosis citation only, Jun. 24-27, 1992; Berlin et al., *Biotechn. Bioengin.: Combin. Chem.* 61; 107-118, 1998; and Richert, *J. Photochem. Photobiol.*, 19:67-69, 1993.

Tissue Collapse and Fibrosis

When the target tissue is the lung, any of the conditioning steps described above can involve or be followed by application of a physiologically compatible composition containing an anti-surfactant (i.e., an agent that increases the surface tension of fluids lining the alveoli).

An antisurfactant may include one or more lipids. An anti-surfactant may include one or more phospholipids and/or fatty acids. An antisurfactant may include, but is not limited to, one or more of phosphatidylcholine, lysophosphatidylcholine, phosphatidylglycerol, palmitic acid, and/or arachidic acid.

In one embodiment, the composition may be formulated as a solution or suspension and includes fibrin or fibrinogen. An advantage of administering these substances is that they can each act not only as anti-surfactants, but can participate in the adhesive and fibrotic process as well. Optionally, the targeted region can be lavaged with saline to reduce the amount of surfactant that is naturally present prior to administration of the anti-surfactant composition.

Adhesives can be applied to tissue mating surfaces and/or target vessels before the surfaces are brought into contact. The adhesive may be applied to either or both of the mating surfaces and may be a one-part or a two-part adhesive. Further, the curing of the adhesive may be activated by light or heat energy. The adhesive may be applied as a liquid or as a solid film. Adhesive materials may include collagen, albumin, fibrin, hydrogel and glutaraldehyde. An adhesive may include one or more biological adhesives (e.g. a biological hydrogel), synthetic adhesives (e.g. a synthetic hydrogel), or a combination thereof. For example, adhesives may include a cyano-acrylates, polyvinyl alcohol borate, alginate, and other adhesive compositions. An adhesive may include two components that polymerize upon contact (one of the components may be an activator). In one embodiment, one or more adhesive components may be mixed or activated in situ so that polymerization or gel formation occurs in situ. In another embodiment, one or more adhesive components may be mixed or activated outside the body shortly before the adhesive is introduced into the target lung region.

Fibrinogen-Based Solutions

Fibrinogen can function as an anti-surfactant because it increases the surface tension of fluids lining the alveoli, and it also can finction as a sealant or adhesive because it can participate in a coagulation cascade in which it is converted to a fibrin monomer that is then polymerized and cross-linked to form a stable mesh, permanently stabilizing collapsed regions. Fibrinogen, which has also been called Factor I, represents about 2-4 gfL of blood plasma protein, and is a monomer that consists of three pairs of disulfide-linked polypeptide chains designated $(A\alpha)_2$, $(B\beta)_2$, and $\gamma_2$. The "A" and "B" chains represent the two small N-terminal peptides and are also known as fibrinopeptides A and B, respectively. The cleavage of fibrinogen by thrombin results in a compound termed fibrin I, and the subsequent cleavage of fibrinopeptide B results in fibrin II. Although these cleavages reduce the molecular weight of fibrinogen only slightly, they nevertheless expose the polymerization sites. In the process of normal clot formation, the cascade is initiated when fibrinogen is exposed to thrombin, and this process can be replicated in the context of lung volume reduction when fibrinogen is exposed to an activator such as thrombin, or an agonist of the thrombin receptor, in an aqueous solution containing calcium (e.g. 1.5 to 5.0 mM calcium).

The fibrinogen-containing composition may include 0.1-20% fibrinogen, 0.5-5%, 5-10%, 10-15%, 3-12%, or other percent range of fibrinogen. In one embodiment, a composition may include approximately 10% fibrinogen in saline (e.g., 0.9% saline) or another physiologically acceptable aqueous solution. The volume of anti-surfactant administered will vary, depending on the size of the region of the lung, as estimated from review of computed tomagraphy scanning of the chest. For example, the targeted region can be lavaged with 10-100 mls (e.g., 50 mls) of fibrinogen solution (10 mg/ml). To facilitate lung collapse, the target region can be exposed to (e.g., rinsed or lavaged with) an unpolymerized solution of fibrinogen and then exposed to a second fibrinogen solution that is subsequently polymerized with a fibrinogen activator (e.g., thrombin or a thrombin receptor agonist).

The anti-surfactant can contain fibrinogen that was obtained from the patient before the non-surgical lung reduction procedure commenced (i.e., the anti-surfactant or adhesive composition can include autologous fibrinogen). The use of an autologous substance is preferable because it eliminates the risk that the patient will contract some form of hepatitis (e.g., hepatitis B or non A, non B hepatitis), an acquired immune deficiency syndrome (AIDS), or other blood-transmitted infection. These infections are much more likely to be contracted when the fibrinogen component is extracted from pooled human plasma (see, e.g., Silberstein et al., *Transfusion* 28:319-321, 1988). Human fibrinogen is commercially available through suppliers known to those of skill in the art or may be obtained from blood banks or similar depositories.

Polymerization of fibrinogen-based anti-surfactants can be achieved by adding a fibrinogen activator. These activators are known in the art and include thrombin, batroxobin (such as that from *B. Moojeni, B. Maranhao, B. atrox, B. Ancrod,* or *A. rhodostoma*), and thrombin receptor agonists. When combined, fibrinogen and fibrinogen activators react in a manner similar to the final stages of the natural blood clotting process to form a fibrin matrix. More specifically, polymerization can be achieved by addition of thrombin (e.g, 1-10 units of thrombin per ng of fibrinogen). If desired, 1-5% (e.g., 3%) factor XIIIa transglutaminase can be added to promote cross-linking.

In addition, one or more of the compositions applied to achieve lung volume reduction (e.g., the composition containing fibrinogen) can contain a polypeptide growth factor. Numerous factors can be included. Platelet-derived growth factor (PDGF) and those in the fibroblast growth factor and transforming growth factor-β families are preferred. Accordingly, growth factors include, but are not limited to, FGF-1, FGF-2, FGF-4, FGF-7, FGF-10, TGF-beta, PDGF, and insulin-like-growth factor 1 (IGF-1). However, other growth factors (including other FGFs) or combinations of any of the above growth factors also may be used.

For example, the polypeptide growth factor included in a composition administered to reduce lung volume (e.g., the fibrinogen-, fibrinogen activator-, or fibrin-based compositions described herein) can be basic FGF (bFGF), acidic FGF (aFGF), the hst/Kfgf gene product, FGF-5, FGF-10, or int-2. The nomenclature in the field of polypeptide growth factors is complex, primarily because many factors have been isolated independently by different researchers and, historically, named for the tissue type used as an assay during purification of the factor. This complexity is illustrated by basic FGF, which has been referred to by at least 23 different names (including leukemic growth factor, macrophage growth factor, embryonic kidney-derived angiogenesis factor 2, prostatic growth factor, astroglial growth factor 2, endothelial growth factor, tumor angiogenesis factor, hepatoma growth factor, chondrosarcoma growth factor, cartilage-derived growth factor 1, eye-derived growth factor 1, heparin-binding growth factors class II, myogenic growth factor, human placenta purified factor, uterine-derived growth factor, embryonic carcinoma-derived growth factor, human pituitary growth factor, pituitary-defived chondrocyte growth factor, adipocyte growth factor, prostatic osteoblastic factor, and mammary tumor-derived growth factor). Thus, any factor referred to by one of the aforementioned names is within the scope of the invention.

The compositions can also include "functional polypeptide growth factors," i.e., growth factors that, despite the presence of a mutation (be it a substitution, deletion, or addition of amino acid residues) retain the ability to promote fibrosis in the context of lung volume reduction. Accordingly, alternate molecular forms of polypeptide growth factors (such as the forms of bFGF having molecular weights of 17.8, 22.5, 23.1, and 24.2 kDa) are within the scope of the invention (the higher molecular weight forms being colinear N-terminal extensions of the 17.8 kDa bFGF (Florkiewicz et al., *Proc. Natl. Acad. Sci. USA* 86:3978-3981, 1989)).

It is well within the abilities of one of ordinary skill in the art to determine whether a polypeptide growth factor, regardless of mutations that affect its amino acid content or size, substantially retains the ability to promote fibrosis as would the full length, wild type polypeptide growth factor (i.e., whether a mutant polypeptide promotes fibrosis at least 40%, preferably at least 50%, more preferably at least 70%, and most preferably at least 90% as effectively as the corresponding wild type growth factor). For example, one could examine collagen deposition in cultured fibroblasts following exposure to full-length growth factors and mutant growth factors. A mutant growth factor substantially retains the ability to promote fibrosis when it promotes at least 40%, preferably at least 50%, more preferably at least 70%, and most preferably at least 90% as much collagen deposition as does the corresponding, wild-type factor. The amount of collagen deposition can be measured in numerous ways. For example, collagen expression can be determined by an immunoassay. Alternatively, collagen expression can be determined by extracting collagen from fibroblasts (e.g., cultured fibroblasts or those in the vicinity of the reduced lung tissue) and measuring hydroxyproline.

The polypeptide growth factors useful in the invention can be naturally occurring, synthetic, or recombinant molecules and can consist of a hybrid or chimeric polypeptide with one portion, for example, being bFGF or TGFβ, and a second portion being a distinct polypeptide. These factors can be purified from a biological sample, chemically synthesized, or produced recombinantly by standard techniques (see, e.g., Ausubel et al., *Current Protocols in Molecular Biology,* New York, John Wiley and Sons, 1993; Pouwels et al., *Cloning Vectors: A Laboratory Manual,* 1985, Supp. 1987).

One of ordinary skill in the art is well able to determine the dosage of a polypeptide growth factor required to promote fibrosis in the context of BLVR. The dosage required can vary and can range from 1-100 nM.

In addition, any of the compositions or solutions described herein for lung volume reduction (e.g., the fibrinogen-based composition described above) can contain one or more antibiotics (e.g., ampicillin, gentamycin, cefotaxim, nebacetin, penicillin, or sisomicin, inter alia). The inclusion of antibiotics in therapeutically applied compositions is well known to those of ordinary skill in the art.

Fibrin-Based Solutions

Fibrin can also function as an anti-surfactant as well as a sealant or adhesive. However, in contrast to fibrinogen, fibrin can be converted to a polymer without the application of an activator (such as thrombin or factor XIIIa). In fact, fibrin I monomers can spontaneously form a fibrin I polymer that acts as a clot, regardless of whether they are crosslinked and regardless of whether fibrin I is further converted to fibrin II polymer. Without limiting the invention to compounds that function by any particular mechanism, it can be noted that when fibrin I monomers come into contact with a patient's blood, the patient's own thrombin and factor XIII may convert the fibrin I polymer to crosslinked fibrin II polymer.

Any form of fibrin monomer that can be converted to a fibrin polymer can be formulated as a solution and used for lung volume reduction. For example, fibrin-based compositions can contain fibrin I monomers, fibrin II monomers, des BB fibrin monomers, or any mixture or combination thereof. In some embodiments, the fibrin monomers are not crosslinked.

Fibrin can be obtained from any source so long as it is obtained in a form that can be converted to a fibrin polymer (similarly, non-crosslinked fibrin can be obtained from any source so long as it can be converted to crosslinked fibrin). For example, fibrin can be obtained from the blood of a mammal, such as a human, and may be obtained from the patient to whom it will later be administered (i.e., the fibrin is autologous fibrin). Alternatively, fibrin can be obtained from cells that, in culture, secrete fibrinogen.

Fibrin-based compositions can be prepared as described in U.S. Pat. No. 5,739,288 (which is hereby incorporated by referenced in its entirety). In some embodiments, firbrin-based compositions contain fibrin monomers having a concentration of no less than about 10 mg/ml. For example, the fibrin monomers can be present at concentrations of from about 20 mg/ml to about 200 mg/ml; from about 20 mg/ml to about 100 mg/ml; and from about 25 mg/ml to about 50 mg/ml. However, in other embodiments, compositions with less than 10 mg/ml of fibrin monomer may be used.

The spontaneous conversion of a fibrin monomer to a fibrin polymer can be facilitated by contacting the fibrin monomer with calcium ions (as found, e.g., in calcium chloride, e.g., a 3-30 mM $CaCl_2$ solution). Except for the first two steps in the intrinsic blood clotting pathway, calcium ions are required to promote the conversion of one coagulation factor to another. Thus, blood will not clot in the absence of calcium ions (but, in a living body, calcium ion concentrations never fall low enough to significantly affect the kinetics of blood clotting; a person would die of muscle tetany before calcium is diminished to that level). Calcium-containing solutions (e.g., sterile 10% $CaCl_2$) can be readily made or purchased from a commercial supplier.

The fibrin-based compositions described here can also include one or more polypeptide growth factors that promote fibrosis (or scarring) at the site where one region of the collapsed lung adheres to another. Numerous factors can be used including those in the fibroblast growth factor and transforming growth factor-β families. Polypeptide growth factors suitable for inclusion with fibrin-based compositions include all of those (described above) that are suitable for inclusion with fibrinogen-based compositions.

Solutions that Include Components of the Extracellular Matrix

The anti-surfactants described above, including fibrin- and fibrinogen-based solutions, can also contain one or more agents that enhance the mechanical and/or biological properties of the solutions. As described above, such solutions can be used to lavage (i.e. to wash out) the tissue or to adhere one portion of the tissue to another.

Useful agents include those that: (1) promote fibroblast and mononuclear cell chemotaxis and collagen deposition in a self-limited and localized manner; (2) dampen the activity of alveolar epithelial cells, either by inhibiting their ability to express surfactant, which promotes reopening of target regions, or by promoting epithelial cell apoptosis, which causes inflammation; (3) promote epithelial cell constriction, which decreases blood flow to target regions, thereby minimizing mismatching between ventilation and perfusion and any resulting gas exchange abnormalities. More specifically, solutions containing components of the extracellular matrix (ECM), endothelin-1, and/or pro-apoptotic reagents can be used. Suitable pro-apoptotic agents include proteins in the Bcl-2 family (e.g., Bax, Bid, Bik, Bad, and Bim and biologically active fragments or variants thereof), proteins in the caspase family (e.g., caspase-3, caspase-8, caspase-9, and biologically active fragments or variants thereof), and proteins in the annexin family (e.g. annexin V, or a biologically active fragment or variant thereof). Solutions containing several of these agents have been tested. The first agents to be tested were selected based on their biological attributes, their biophysical effects on gel behavior, their solubility in aqueous solutions (under physiological conditions), and cost. Those of ordinary skill in the art will be able to recognize and use comparable agents without resort to undue experimentation.

The agents selected for use initially were chondroitin sulfate A and C, low and high molecular weight hyaluronic acid, fibronectin, medium and long chain poly-L-lysine, and the collagen dipeptide proline-hydroxyproline.

Chondroitin sulfate (CS) is an ECM component of the glycosaminoglycan (GAG) family. It is a sulfated carbohydrate polymer composed of repeating dissaccharide units of galactosamine linked to glucuronic acid via a beta 1-4 carbon linkage. CS is not found as a free carbohydrate moiety in vivo, but rather is bound to core proteins of various types. As such, it is a component of several important ECM proteoglycans including members of the syndecan family (syndecan 1-4), leucine-rich family (decorin, biglycan), and the hyaluronate binding family (CD44, aggrecan, versican, neuroncan). These CS-containing proteoglycans function in the binding of cell surface integrins and growth factors. CS-containing proteoglycans may function within the lung as scaffolding for collagen deposition by fibroblasts. Thus, ECM components within the glycosaminoglycan family, particularly carbohydrate polymers, are useful in achieving tissue volume reduction (e.g., lung volume reduction carried out bronchoscopically). For example, the addition of chondroitin sulfate A or C at concentrations ranging from 0.05-3.00% has a specific and beneficial effect on both the mechanical and biological properties of fibrin gels. Similarly, solutions useful to lavage and adhere tissue can contain comparable amounts of one or more proteoglycans such as syndecan 1-4, decorin, biglycan, CD44, aggrecan, versican, and neuroncan. In one embodiment, the composition of the invention includes ethanol (e.g., 1-20%) fibrinogen (e.g., 0.01-5.00%), HA (e.g., 0.01-3.00%), FN (e.g., 0.001-0.1%), and CS (e.g., 0.01-1.0%). For example, a useful composition of the invention includes 10% ethanol, 0.5% fibrinogen, 0.3% HA, 0.01% FN, and 0.1% CS.

Hyaluronic acid (HA), like CS, is a polysaccharide, consisting of repeating units of glucuronic acid and N-acetylglucosamine joined by a beta 1-3 linkage. However, unlike CS and other GAGs, HA functions in vivo as a free carbohydrate and is not a component of any proteoglycan family. HA is a large polyanionic molecule that assumes a randomly coiled structure in solution and, because of its self-aggregating properties, imparts high viscosity to aqueous solutions. It supports both cell attachment and proliferation. In addition, HA is believed to promote monocyte/macrophage chemotaxis and to stimulate cytokine and plasmin activator inhibitor secretion from these cells. Thus, polysaccharides that include repeating units of, for example, glucuronic acid and N-acetyl-glucosamine, are useful in achieving tissue volume reduction (e.g., lung volume reduction carried out bronchoscopically). For example, the addition of either high or low MW HA at concentrations ranging from 0.05-3.00% will have a specific and beneficial effect on both the mechanical and biological properties of fibrin gels.

Fibronectin (Fn) is a widely distributed glycoprotein present within the ECM. It is present within tissues as a heterodimer in which the subunits are covalently linked by a pair of disulfide bonds near the carboxyl terminus. Fn is divided into several domains, each of which has a distinct function. The amino terminal region has binding sites for fibrin, heparin, factor XIIIa, and collagen. Fn has a central cell-binding domain, which is recognized by the cell surface integrins of macrophages, as well as fibroblasts, myofibroblasts, and undifferentiated interstitial cells. Fn's primary function in vivo is as a regulator of wound healing, cell growth, and differentiation. Fn can promote binding and chemotaxis of fibroblasts. It can also act as a cell cycle competency factor allowing fibroblasts to replicate more rapidly when exposed to appropriate "progression signals." In vitro, Fn promotes fibroblast migration into plasma clots. In addition, Fn promotes alterations in alveolar cell phenotype that result in a decrease in surfactant expression. Thus, Fn molecules that promote tissue collapse and scar formation are useful in achieving tissue volume reduction (e.g, lung volume reduction carried out bronchoscopically). Fn isoforms generated by alternative splicing are useful, and addition of lysophosphatidic acid, or a salt thereof, can be added to Fn-containing solutions to enhance Fn binding. For example, the addition of a Fn at a concentration ranging from 0.05-3.00% will have a specific and beneficial effect on both the mechanical and biological properties of fibrin gels used, for example, in BLVR. Poly-L-lysine (PLL) is commonly used in cell culture experiments to promote cell attachment to surfaces, and it is strongly positively charged. Despite its large size, it dissolves readily in the presence of anionic polysaccharides, including HA and CS. Thus, PLL, HA, and CS may be used in combination in solutions to lavage, destabilize, and adhere one portion of a tissue to another. The studies described below explore the possibility that PLL in a fibrin network containing long chain polysaccharides generates ionic interactions that make fibrin gels more elastic and less prone to breakage during repeated stretching. PLL can also promote hydration and swelling once matrices are formed. Thus, a particular advantage of using solutions containing PLL for lung volume reduction is that such solutions make it even less likely that the resulting matrices will be dislodged from the airway. PLL having a molecular weight between 3,000 and 150,000 can be used at concentrations of 0.1 to 5.0%. However, in some embodiments, higher or lower concentrations may be used.

The di-peptide proline-hydroxyproline (PHP) is common to the sequence of interstitial collagens (type I and type III). Collagen-derived peptides may act as signals for promoting fibroblast in-growth and repair during the wound healing process. The PHP di-peptide, at concentrations ranging from 2.5-10.0 mM, is as effective as type I and type II collagen fragments in promoting fibroblast chemotaxis in vitro. Thus, PHP di-peptides are useful in achieving tissue volume reduction (e.g., lung volume reduction carried out bronchoscopically). For example, the addition of PHP di-peptides at concentrations ranging from 0.05-3.00% will have a specific and beneficial effect on both the mechanical and biological properties of fibrin gels.

The addition of ECM components to washout solutions and fibrin gels may promote tissue collapse and scarring by modulating the activity of interstitial fibroblasts and lung macrophages. Disruption of intact epithelium tends to promote permanent atelectasis and scarring. Thus, it can be useful to expose the alveolar epithelium to agents that cause inflammation and trigger an "ARDS-like" response. Of course, administration of such agents must be carefully controlled and monitored so that the amount of inflammation produced is not hazardous. Alternatively, tissue repair and volume reduction can be facilitated by the addition of agents that promote epithelial cell apoptosis, "programmed cell death," without extensive necrosis and inflammation. These agents would cause a loss of alveolar cell function without inflammation. One way to produce such a response is by administering sphingomyelin (SGM), a lipid compound that is taken up by certain cell types and enzymatically converted by sphingomyelinase and ceramide kinase to ceramide-I-phosphate, a key modulator of programmed cell death. The application of SGM is also likely to inhibit surfactant, since SGM has anti-surfactant activity in vitro. SGM could be administered in the antisurfactant washout solution, where it could act specifically on the epithelial surface to destabilize the local surface film and cause epithelial cell death without inflammation. Solutions useful for repairing air leaks in pulmonary tissue or for performing BLVR can contain SGM, or a biologically active variant thereof, at concentrations ranging from 0.05-15.00% (e.g., 0.1, 0.5, 1.0, 2.0, 2.5, 5.0, 7.5, 10.0, 12.0, 13.0, 14.0, or 14.5%) or higher or lower concentrations.

The efficacy of BLVR can also be enhanced by modulating the endothelial cell response. For example, transient vasoconstriction can be achieved by including epinephrine or norepinephrine in the washout solution. Sustained endothelial modulation could be achieved by inclusion of one of the endothelins, a family of cytokines that promotes vasoconstriction and acts as a profibrotic agent. Endothelin-1, endothelin-2, or endothelin-3 can be used alone or in combination. Thus, solutions of the invention can also include a vasoactive substance such as endothelin, epinephrine, or norepinephrine (at concentrations ranging from 0.01-5.00% or at higher or lower concentrations), or combinations thereof. The advantage of including one or more vasoactive substances is that they favorably modulate the vascular response in the target tissue and this, in turn, reduces ventilation perfusion mismatching, improves gas exchange, and, simultaneously, promotes scar formation.

Application of Fibrin-Based, Fibrinogen-Based and ECM-Containing Compositions Following Lung Collapse Following pre-conditioning by one of the methods described above, a targeted region of the lung can be collapsed by exposure to one of the fibrin-based, fibrinogen-based, and ECM-containing compositions described above; in addition, these substances can also be applied to adhere one region of the lung to another and to promote fibrosis when the collapse has been induced by other means. For example, the fibrin-based, fibrinogen-based, and ECM-containing compositions described above can be applied after the lung collapses from blockage of airflow into or out of the targeted region. Such blockage can be readily induced by, for example, inserting a bronchoscope into the trachea of an anesthetized patient, inserting a balloon catheter through the bronchoscope, and inflating the balloon so that little or no air passes into the targeted region of the lung. A valve or any other occlusion device also may be used. Collapse of the occluded region after the lung is filled with absorbable gas would occur over approximately 5-15 minutes, depending on the size of the region occluded. Alternatively, a fibrinogen- or fibrin-based solution (e.g a fibrinogen- or fibrin-based solution that contains a polypeptide growth factor), as well as solutions that contain components of the ECM (such as those described herein), ECM-like agents (such as PLL and PHP), vasoactive substances (ie., substances that cause vasoconstriction), and pro-apoptotic factors (e.g., proteins in the Bcl-2, caspase, and annexin families) can be applied after the lung is exposed to another type of anti-surfactant (e.g., a non-toxic detergent).

Identifying and Gaining Access to a Target Region of the Lung

Once a patient is determined to be a candidate for BLVR, the target region of the lung can be identified using radiological studies (e.g., chest X-rays) and computed tomography scans. When the LVR procedure is subsequently performed, the patient is anesthetized and intubated, and can be placed on an absorbable gas (e.g., at least 90% oxygen and up to 100% oxygen) for a specified period of time (e.g., approximately 30 minutes). The region(s) of the lung that were first identified radiologically are then identified bronchoscopically.

Suitable bronchoscopes include those manufactured by Pentax, Olympus, and Fujinon, which allow for visualization of an illuminated field. The physician guides the bronchoscope into the trachea and through the bronchial tree so that the open tip of the bronchoscope is positioned at the entrance to target region (i.e., to the region of the lung that will be reduced in volume). The bronchoscope can be guided through progressively narrower branches of the bronchial tree to reach various subsegments of either lung. For example, the bronchoscope can be guided to a subsegment within the upper lobe of the patient's left lung.

The balloon catheter may then be guided through the bronchoscope to a target region of the lung. When the catheter is positioned within the bronchoscope, the balloon is inflated so that material passed through the catheter will be contained in regions of the lung distal to the balloon. This is particularly useful in the methods of the present invention, which include the introduction of liquids into the selected region of the lung.

Methods that Employ Physical Barrier to Cause Collapse in a Target Region.

Methods of the invention can be used alone or in combination with devices that can be inserted to block one or more airways. For example, methods of the invention can be used to block collateral flow, thereby allowing a stent, valve, or other device to be used effectively to collapse a target region of the lung.

In addition, methods of the invention can be used to damage the epithelial cell layer in target regions of the lung and thereby promote collapse and/or fibrosis. Alternatively, methods for damaging the epithelial cells (or other cells described herein) can be combined with subsequent application of a hydrogel as described herein to promote collapse and/or fibrosis of the target region.

Formulations and Use

The compositions of the present invention can be formulated as dry powders, and they may be reconstituted before use. For example, a composition having biophysical characteristics appropriate for treating emphysema can be formulated as a dry powder and reconstituted with water (e.g., sterile, preservative-free water) prior to administration. When possible, and whenever preservatives or anti-microbial agents are omitted, the compositions should be reconstituted using full aseptic technique. When full aseptic technique cannot be ensured, reconstitution should take place immediately before use and any unused suspension should be discarded.

The compositions can be supplied in the form of a kit that, in addition to the compositions, contains, for example, a vial of sterile water or a physiologically acceptable buffer. Optionally, the kit can contain an atomizer system to generate particulate matter (atomizers are presently commercially available) and instructions for use and other printed material describing, for example, possible side effects. Other methods of administration are suitable, and they include all those presently considered appropriate and effective for photodynamic therapy. A direct and effective method is instillation of the surface film into the lung through the trachea. The compositions can be administered as a liquid solution in water or buffered physiological solutions (e.g., saline), and can be administered over a period of several minutes (e.g., 5-15 (e.g., ten) minutes).

A useful mechanism for delivery of the powder into the lungs of a patient is through a portable inhaler device suitable for dry powder inhalation. Many such devices, typically designed to deliver anti-asthmatic agents (e.g., bronchodilators and steroids) or anti-inflammatory agents into the respiratory system are commercially available. The device can be a dry powder inhaler, which can be designed to protect the powder from moisture and to minimize any risk from occasional large doses. In addition, the device can protect the surface film from light and can provide one or more of the following: a high respirable fraction and high lung deposition in a broad flow rate interval; low deviation of dose and respirable fraction; low retention of powder in the mouthpiece; low adsorption to the inhaler surfaces; flexibility in dose size; and low inhalation resistance. The inhaler can be a single-dose inhaler or a multi-dose inhaler.

The compositions, in powder form, can be manufactured in several ways, using conventional techniques. One can, if desired, micronize the active compounds (e.g., one or more of the lipids). One can also use a suitable mill (e.g., a jet mill) to produce primary particles in a size range appropriate for maximal deposition in the lower respiratory tract (i.e., under 10 µM). For example, one can dry mix lipids and other components of the surface film (e.g., proteins or peptides) and a carrier (where appropriate) and micronize the substances together. Alternatively, the substances can be micronized separately and then mixed. Where the compounds to be mixed have different physical properties (e.g., hardness or brittleness), resistance to micronization varies, and each compound may require a different pressure to be broken down to suitable particle sizes.

It is also possible to dissolve the components first in a suitable solvent (e.g., sterile water or PBS) to obtain mixing on the molecular level. When this is done, one can adjust the pH value to a desired level. To obtain a powder, the solvent should be removed by a process that allows the components of the surface film to retain their biological activity. Suitable drying methods include vacuum concentration, open drying, spray drying, and freeze-drying. After being dried, the solid material can, if necessary, be ground to obtain a coarse powder, and further, if necessary, micronized.

In addition, and if desired, the micronized powder can be processed to improve the way in which it flows through and out of inhaler (or other) devices. For example, the powder can be processed by dry granulation to form spherical agglomerates with superior handling characteristics. In that case, the device would be configured to ensure that no substantial agglomerates exit the device. A possible advantage of this process is that the particles entering the respiratory tract of the patient are largely within the desired size range.

The delivery apparatus can also be a nebulizer that generates an aerosol cloud containing the components of the surface film. Nebulizers are known in the art and can be a jet nebulizer (air or liquid; see, e.g., EP-A-0627266 and WO 94/07607), an ultrasonic nebulizer, or a pressure mesh nebulizer. Ultrasonic nebulizers, which nebulize a liquid using ultrasonic waves usually developed with an oscillating piezoelectric element, take many forms (see, e.g., U.S. Pat. Nos. 4,533,082 and 5,261,601, and WO 97/29851). Pressure mesh nebulizers, which may or may not include a piezoelectric element, are disclosed in WO 96/13292.

Figure 14A:
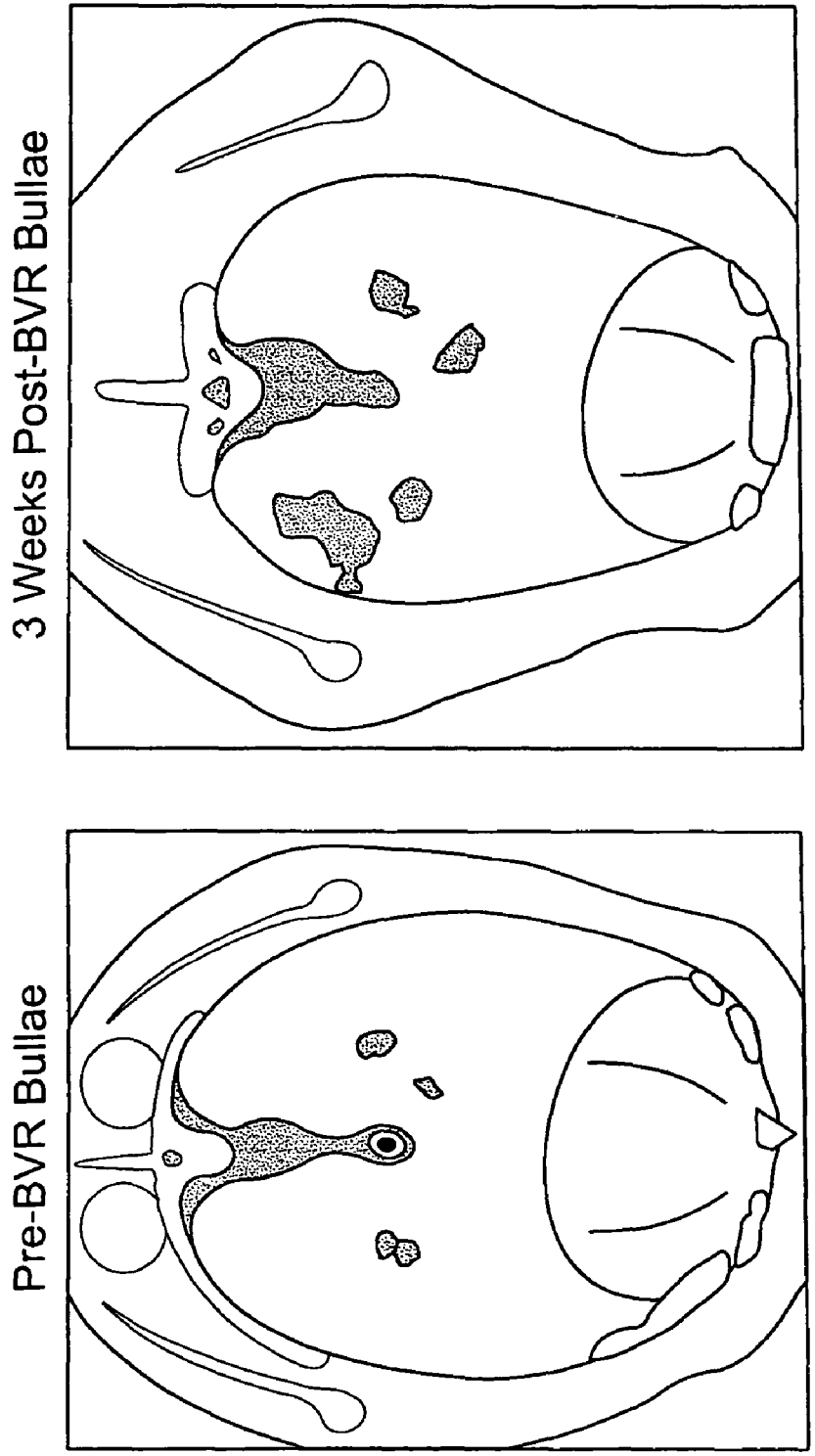

Nebulizers, together with dry powder and metered dose inhalers, are commonly used to deliver substances to the pulmonary air passages. Metered dose inhalers are popular, and they may be used to deliver medicaments in a solubilized form or as a dispersion (the propellant system historically included one or more chlorofluorocarbons, but these are being replaced with environmentally friendly propellants). Typically, these inhalers include a relatively high vapor pressure propellant that forces aerosolized medication into the respiratory tract upon activation of the device. To the contrary, dry powder inhalers generally rely entirely on patients' inspiratory efforts to introduce a medicament in a dry powder form to the lungs. Nebulizers form a medicament aerosol by imparting energy to a liquid solution. More recently, therapeutic agents have been delivered to the lungs during liquid ventilation or pulmonary lavage using a fluorochemical medium.

In a preferred embodiment, the liposomal photophrin compositions of the present invention are delivered to a targeted region of the lung via a bronchoscope.

Although we describe here the detailed methodology for use of a trypsin-based enzymatic pre-conditioning approach, application of any of these alternative epithelial cell preconditioning procedures would be performed in a similar fashion. For example, use of a detergent, a polycation, mechanical brushing, ultrasound energy, thermal energy, or photodynamic therapy could each be administered prior to hydrogel (e.g., fibrin hydrogel) administration. While the specific technique utilized would vary depending upon the approach, the concepts are generally the same and can be expressed as follows: first, remove at least some of the epithelial lining of the target region to facilitate fibroblast proliferation and ingrowth; and second, inject the target region with a hydrogel that facilitates attachment, chemotaxis, growth of, and collagen deposition by resident fibroblasts. In some embodiments, a detergent and/or a polycationic preparation may be administered along with a hydrogel.

The present invention is further illustrated by the following examples, which are provided by way of illustration and should not be construed as limiting. The contents of all references, published patent applications and patents cited throughout the present application are hereby incorporated by reference in their entirety. A number of embodiments of the invention have been described. Nevertheless, it will be understood that various modifications may be made without departing from the spirit and scope of the invention.

EXAMPLES

Certain aspects of the invention are exemplified in the following non-limiting examples.

Example 1

Enzvmatic-Pre-Conditioning

We examined the safety and utility of trypsin preconditioning for BVR in a group of seven sheep with emphysema generated by prior exposure to papain inhalation. This large animal model of emphysema is one with which we have extensive prior experience. The model possesses many characteristics of human emphysema, the primary target disease for which BVR has been developed as therapy. In this study, the presence of significant emphysema was demonstrated 2 weeks following serial papain exposure by documenting: (1) a significant increase in lung volumes measured by plethysmography, demonstrating hyperinflation as a result of tissue damage, (2) a significant decrease in tissue density expressed in Houndsfield units as measured by CT scanning; and (3) imaging studies demonstrating readily identifiable regions of bullae formation. The experimental results are summarized in FIGS. 7, 8, and 9.

To ensure effective epithelial cell removal, and exposure of the underlying fibroblasts that are the primary cells responsible for scar formation, a critical step in BVR, we employed a trypsin-based solution instilled bronchoscopically into specific targeted regions of lung. In this experiment, the solution took between 1 and 3 minutes to promote epithelial cell dislodgement. Results presented here were accomplished utilizing a protocol in which the bronchoscope was wedged into position, 15 mls of solution was instilled into a 5th-6th generation airway, and the mixture was left in place for 90 seconds. Suction at −120 cm $H_2O$ was then applied to remove as much of the residual solution as possible. In most instances, returns averaged between 40-50% of instilled volume. A second saline-based washout solution, containing serum and aprotinin, both of which act to neutralize the enzymatic effects of trypsin, was then injected into the same target area. This was left in place for 30 seconds, and suction was then reapplied to remove as much of the mixture as possible. The fibrin based hydrogel was then injected and polymerized within this target area to help maintain a localized reaction, and serve as a substrate for fibroblast attachment and growth as a initial step towards permanent scarring (FIG. 10).

Results: The procedure was uniformly well tolerated by all animals. Trypsin pre-conditioning was associated with no bleeding, excessive coughing, marked hypoxemia, or immunological reactions. Three of seven experienced a mild fever that lasted less than 48 hours. All recovered rapidly from the intervention without the need for immediate or long term oxygen therapy. None required antibiotics, antiinflammatory agents, or bronchodilator treatment.

Results of physiology studies for animals undergoing BVR with trypsin pre-conditioning are shown in FIGS. 11, 12 and 13. Compared to baseline, post-papain animals demonstrated a marked increase in airway resistance and lung volumes. At normal respiratory frequencies, total lung resistance (the sum of airway and tissue components) was increased 40±9%, and airway resistance was increased 75±16% (FIG. 11, lung impedance). Total lung capacity (TLC), the total volume within the lung, increased 10±3%, the residual volume (RV), the trapped gas within the lung, decreased 66±21%, and vital capacity (VC), the functional volume within the lung increased 11±4% (FIG. 12, lung volumes including VC). The inter-relationship between chest wall and lung mechanics that ultimately determines the static properties of the respiratory system are summarized in the Campbell diagram (FIG. 13). Emphysema had no signifficant impact on either active or passive chest wall mechanics, but caused a significant increase in both TLC and RV. The resulting hyper-inflation caused a decrease in recoil pressures at full inflation from 16.4 cm $H_2O$ to 8.9 cm $H_2O$.

Post BVR studies were performed at 1 and 3 months. The physiological parameters measured are summarized in the table presented as FIG. 15. At both post-treatment time points, a significant reduction in lung volumes was demonstrated. BVR using trypsin pre-conditioning produced significant reductions in TLC (7±2%, p=0.05), RV (30±7%, p=0.01) and RV/TLC (25±6%, p=0.01) ratio with corresponding increases in VC (11±4%, p=0.03) and recoil pressures at TLC (69±25 14%, p=0.007) were decreased. Responses observed at 1 month were sustained at 3 month follow-up demonstrating that BVR treatment using this approach generates what appears to be permanent physiological benefit. FIG. 14 shows an example of an animal with heterogeneous emphysema that had developed a bullous lesion in response to papain instilled bronchoscopically. The bullae located in the right upper dorsal lobe (bronchus R4) measured 5×3×7 cm prior to treatment. At 1 month post BVR, the lesion was reduced in size to 3×2×2 cm in dimensions. At 3 month follow-up, the bullae demonstrated complete closure, with expansion of adjacent normal lung into the region previously occupied by the bullae.

At sites of BVR where poorly localized, homogeneous emphysema had existed, BVR using trypsin pre-conditioning produced localized scars that were readily identified on CT scan, and occurred specifically and exclusively at those sites documented to have undergone BVR injection. Example images of BVR sites treated for presence of diffuse emphysema are also shown in FIG. 14.

At 3-month follow-up, all animals appeared well, were gaining weight, and appeared to have normal activity levels.

Example 2

Enzyme Pre-Conditioning Solution and Neutralizing Solution

Enzyme pre-conditioning solution: In one formulation, a trypsin preconditioning solution consists of an aqueous buffered solution containing 500 BAEE units purified virus free porcine pancreatic trypsin/ml, and 180 mg 4Na-EDTA/ml in pH 7.4 Delbecco's phosphate buffered saline. Although the trypsin source used in this application was porcine, any of multiple sources would be acceptable including human sources and other animal sources. Trypsin was specifically selected for use here because there is extensive experience utilizing this enzyme in experimentation, it has been shown to have minimal direct cellular toxicity, and is inexpensive to obtain commercially. All of our studies have been performed utilizing trypsin. However, any of several different enzymes with similar characteristics could potentially be utilized for this purpose. Trypsin is a serine protease; multiple enzymes of this class are available commercially, including chymotrypsin, elastase, any of numerous matrix metalloproteinases, or other serine proteases, as disclosed above. Any of these could be used in a formulation for pre-BVR conditioning.

Enzyme "neutralizing" solution: Since each of these enzymes are proteases and have the potential for not only "loosening" epithelial cells as desired but also for damaging underlying tissue structures, we have chosen to neutralize the trypsin washout preparation as an additional safety step during BVR. The results reported above therefore reflect combining trypsin pre-conditioning with neutralization washout.

The neutralizing solution was designed to inactivate serine protease activity and interface well with subsequent instillation of fibrin hydrogel. The composition of the neutralizing solution is as follows: 10% fetal bovine serum; 0.5 mg/ml tetracycline or 1 mg/ml Ciprofloxacin or 1 mg/ml Clindamycin or 0.5 mg/ml Ancef; and 5 mM $CaCl_2$ dissolved in standard RPMI 1640 cell culture media without glutamine or phenol red, and at pH 7.5.

Specifics of Method of Application:

Prolonged exposure of the lung epithelial surface to trypsin solutions could, in theory, result in tissue damage, and thus a specific protocol for trypsin solution instillation has been developed to limit exposure time. First the bronchoscope is wedged into a specific target region of lung. Given the diameter of the scope for use in human BVR application will be 3-4 mm in diameter, this is likely to correspond to a sub-segmental bronchus. The area subtended by the scope, which corresponds to approximately 5% of total lung volume, is rinsed with 15 mls of enzymatic washout solution. The solution is injected into the target region through the channel of the bronchoscope and left in place for 90 seconds. Then, continuous suction is applied for 1-2 minutes to remove as much of the solution as possible. Thereafter, the neutralizing solution is injected in similar fashion, left in place for 60 seconds, and then suctioned out. The target zone is then ready to be injected with fibrin hydrogel. Such methods can also be used to limit exposure of cells or tissue to detergent solutions described herein.

Example 3

Techniques for Evaluating Different Lung Volume Reduction Methods and Compositions This example provides certain techniques that were be used to evaluate different therapeutic compositions and methods described in Examples 4 and 5. However, these techniques are not limiting and other or additional techniques may be used.

The bronchoscopic lung volume reduction (BLVR) experiments described in Examples 4 and 5 were performed in sheep. Animals were under general anesthesia and supported on mechanical ventilation. Animals received intravenous propofol (Propoflo, Abbott Labs) at 1 mg/kg/hr and intravenous crystalloid fluid (isotonic saline) at 5 mg/kg/hr. Heart rate and rhythm, body temperature, peripheral oxygen saturation levels, peak airway pressures, and tidal volumes were monitored throughout the study.

BLVR procedures were performed using a dual lumen catheter. Test treatments were administered to individual animals in accordance with treatment group assignments as listed in the following examples. Each treatment was performed in identical fashion. For each target region being treated, following secure positioning of the bronchoscope in wedge position, 10 ml of a primer solution was delivered through a channel of the scope by injection through a 10 ml catheter. The primer solution was left in place for 2 minutes. Continuous suction (120-140 cm H2O) was then applied for 1 minute to remove as much reagent as possible. Subsequently, 10 ml of washout solution was injected in similar fashion. The washout solution was left in place for 30 seconds, followed by application of suction for an additional minute to remove residual debris and reagents, and to simultaneously promote collapse. A dual-lumen catheter (1.9 mm O.D.) was then introduced through the instrument channel of the scope, and advanced distally 1-2 cm into the pre-selected treatment site. Fibrinogen and thrombin solutions were injected simultaneously through separate channels of the catheter to produce a hydrogel in situ. The scope was left in place for 30 seconds after delivery of the hydrogel to ensure complete polymerization. The scope was then repositioned at the next treatment site, and the process of primer, washout, and hydrogel administration was repeated. The location of the sub-segments targeted for treatment and visual confirmation of hydrogel polymerization at each of those sub-segments was recorded for every animal. Twelve sites (seven on the right and five on the left) distributed throughout the lungs were treated.

Spiral CT chest scans were obtained at baseline, immediately post-treatment, and at 4-6 weeks post-treatment. CT scans were evaluated for evidence of pneumothorax, abscess formation, or other complications of BLVR, and were scored for the presence of scarring (0=no infiltrate; 1=poorly delineated; low density infiltrate; 2=poorly delineated, low density infiltrate with some denser areas; and 3=well-delineated, dense infiltrate).

Pulmonary function measurements were made at baseline, immediately post-treatment, and at 4-6 weeks post-treatment. In some experiments, only measurements of respiratory resistance (R) and elastance (E) were measured, rather than a full battery of pulmonary function tests, since these two parameters can be measured without prolonged or repeated anesthesia, and provide a useful, yet simple-to-measure index of the physiological response to treatment. In some experiments, lung volume measurements were made at baseline and at the end of the study following BLVR treatment in awake and standing animals. A 2 liter reservoir bag was filled with a known volume of 10% helium balanced air, and connected to a facemask using a three-way valve. At end exhalation, the valve was turned to allow each animal to breath so as to equilibrate with the helium mixture. After 45 seconds of rebreathing, the concentration of helium in the bag was measured using an infrared detector. Lung volume was determined from the initial and final concentrations of helium in the bag, and the volume of helium the animal was made to rebreath.

All animals were humanely euthanized at after 4-6 weeks via sodium pentobarbital overdose (100 mg/kg). Euthanasia was performed in accordance with accepted AVMA guidelines. Following euthanasia, animals were exsanguinated and a complete examination of the external surfaces of the body, all orifices, and the thoracic and abdominal cavities was performed. The heart and lungs were removed en bloc. An endotracheal tube was secured in the trachea, and the lungs were inflated to 2 liters to allow easy visual detection of sites of BLVR treatment. Tissue samples from BLVR treatment sites and non-treated sites were excised and fixed in 10% buffered formalin. Liver, kidney, spleen, and heart were examined in situ. Samples were fixed in 10% buffered formalin. Certain samples were stained with hematoxylin and eosin and evaluated for the presence of scar tissue and any evidence of a toxic reaction.

Vital signs (temperature, heart rate, respiratory rate), oxygen saturation, and Basal Attitude/Activity Response score (BAR) was assessed at baseline, daily for 3 days after treatment, and weekly thereafter. BAR is a semi-quantitative scoring system that assigns a score of 2 if the animal is bright, alert, and responsive, a score of 1 if the animal is quiet, alert, and responsive, and a score of 0 if the animal displays decreased clinical responsiveness or signs of depression. Values of 2 and 1 are considered normal in clinical practice, while a value of 0 indicates a clinical problem.

Where appropriate, comparison of outcome variables at baseline and following BLVR treatment was performed by t-test analysis. Statistical significance was defined as a $p<0.05$. CT scan score values were treated as continuous variables for statistical comparison.

Example 4

Evaluating Certain Lung Volume Reduction Methods and Compositions

In this experiment, seven different types of BLVR test treatments were examined, and compared to a standard BLVR treatment that served as a control. Test treatments differed from standard treatment in that one or more specific system components were removed.

Each test treatment was evaluated in 2 healthy sheep at 12 sites distributed throughout both lungs. All BLVR treatments were delivered using a dual lumen catheter system in identical fashion. BLVR treatment at each site required approximately 6-7 minutes to complete, and the entire 12-treatment procedure required approximately 90 minutes to complete. Follow-up was performed for 1 month.

Animals underwent baseline CT imaging and lung physiology testing. After 4 weeks of clinical monitoring, animals had a final set of studies performed, and were autopsied. Tissue samples were processed for histopathology as described herein.

Table 1 shows the different treatment conditions for the different experimental groups.

TABLE 1

| Treatment conditions: | | | | | |
|---|---|---|---|---|---|
| Group | Animals/Group | Primer | Washout | Hydrogel | Follow-Up Period |
| 1. Control | 2 | Standard | Standard | Standard | 1 month |
| 2. CS- | 2 | Standard | Standard | no CS | 1 month |
| 3. PLL- | 2 | Standard | Standard | no PLL | 1 month |
| 4. CS/PLL- | 2 | Standard | Standard | no CS, no PLL | 1 month |
| 5. PBS | 2 | Standard | PBS | PBS solvent | 1 month |
| 6. TCN- | 2 | Standard | Standard | no TCN | 1 month |
| 7. Trypsin- | 2 | PBS | Standard | Standard | 1 month |
| 8. CS/PLL/TCN/Trypsin- | 2 | None | Standard | No CS, PLL, TCN | 1 month |

In this experiment, the standard primer solution was 0.25% trypsin and 0.03% EDTA in PBS. The standard washout solution was 1× RPMI 1640. The standard hydrogel was 3% fibrinogen, 0.1% poly-L-lysine (PLL) (75-150,000 MWt), 0.1% chondroitin sulfate (CS) (50,000 Mwt), and 0.15% tetracycline (TCN) dissolved in RPMI 1640. A 10 ml volume of this solution was mixed in situ with a 1 ml volume of 1,000 units of thrombin in 40 mM $CaCl_2$ for in situ polymerization.

There were no signs of clinical distress, alterations from baseline activity level, or changes in eating patterns in any of the test groups to suggest an adverse response to any of the treatments. Body weights did not change from pre-treatment baseline values. Activity levels remained in the clinically acceptable range for all treatment groups during the course of the study. No animal showed signs of distress or clinical depression. Heart rate did not change from pre-treatment baseline values. Body temperature did not change from pre-treatment baseline values. Respiratory rates did not change from pre-treatment baseline values.

Blood hematology studies were within normal limits for all animals at baseline, immediately post-treatment, and at 1 month post-treatment. Total circulating white blood cell counts, hematocrit levels, and white cell differentials were all within normal limits. Blood chemistry results, including serum BUN and creatinine, serum albumin, and globulin levels were all also within normal limits for all animals at each time point. One animal in Treatment group 7 demonstrated an apparent acute rise in AST immediately following the procedure. This observation may have resulted from a lipemic serum in this animal (as a consequence of the anesthetic Propofol). No other abnormalities in lab studies were noted.

CT Image Assessment of BLVR Responses:

A semi-quantitative scoring system was developed to assess the extent and organization of scar formation on CT imaging for each treatment site as an index of treatment success. Scores were assigned using a simple grading system based on an analysis of a CT image (0=the site appears the same as adjacent lung tissue with no evidence of treatment; 1=the site displays a focal increase in density but does not show a focal, linear, peripheral scar; 2=the site displays a focal, organizing scar with some highly dense areas, and other loosely organized areas; and 3=the site displays a focal, dense, organized peripheral scar). For each animal, a total score was determined by adding up the scores for each treatment site, and dividing by 12. Final scores were generated as an average of the scores reported by three independent reviewers. The maximum possible CT score that can be assigned using this scoring system is a 3 and the lowest is a 0.

CT scores for Treatment Group 2 (no chondroitin sulfate in the Hydrogel), Treatment Group 5 (no tetracycline in the hydrogel) and Treatment Group 7 (no trypsin in the Primer) were nearly equivalent to standard therapy (Treatment Group 1). CT scores for Treatment Group 3 (No poly L lysine in the hydrogel) and Treatment Group 8 (No trypsin, and no CS, PLL, or tetracycline) were reduced by approximately 25% compared to standard treatment, although these differences were not statistically significant. CT scores for Treatment Group 4 (no CS and no PLL in the hydrogel) and Treatment Group 6 (no RPMI 1640 in the washout or hydrogel) were reduced by 50-75% compared to standard treatment, both of which represented statistically significant reductions.

Additional findings observed on CT images included a 1.7 cm thick-walled cavitary lesion in the right cranial lobe of one animal; and a 2.5 cm solid mass-like lesion in the basilar region of the left caudal lobe of another animal. Both animals were in Treatment Group 5 (no tetracycline in the hydrogel).

Necropsy Assessment of BLVR Responses:

A semi-quantitative scoring system was developed to assess the extent and organization of scar formation observed visually on the visceral pleural surface at the time of autopsy as an index of treatment success. Scores were assigned using a simple grading system based on a visual analysis (0=no visible scar is present at the treatment site; 1=a poorly-organized scar, or pleural bleb is present at the site of treatment; and 2=a well-organized scar with puckering of the pleura indicating volume reduction is present at the site of treatment).

For each animal, a total score was determined by adding up the scores for each treatment site, and dividing by 12. Final scores were generated as an average of the scores reported by two independent reviewers. The maximum possible score that can be assigned using this scoring system is a 2 and the lowest is a 0.

Responses to treatment, assessed grossly in terms of both the number of scars observed, and their extent of organization, was similar to controls (standard BLVR treatment) in Treatment Group 7 (no trypsin in the Primer). Treatment Group 2 (no chondroitin sulfate in the Hydrogel), Treatment Group 3 (no poly L lysine in the Hydrogel), and Treatment Group 5 (no tetracycline in the Hydrogel) had scarring response scores that were 20-25% reduced compared to controls, although differences were not statistically significant. Treatment Group 4 (no CS and no PLL in the hydrogel), Treatment Group 6 (no RPMI 1640 in the washout or hydrogel), and Treatment Group 8 (No trypsin, and no CS, PLL, or tetracycline) had scarring response scores that were significantly reduced compared to controls.

Additional necropsy findings in sheep of Treatment Group 5 included: i) three regions of parenchymal necrosis in the lung of one sheep that were grossly consistent with abscesses; and ii) a large mass-like lesion in the left basilar region of the lung of another sheep which, upon dissection, was associated with an encapsulated abscess (this corresponds to the 2.5 cm lesion noted on the CT scan).

Tissue Histopathology:

Paraffin-embedded tissue sections of lung, heart, liver, kidney, and spleen fixed in 10% buffered formalin and stained with hematoxylin and eosin were prepared. Tissues were harvested 1 month following BLVR treatment.

Scar tissue formation, assessed histologically by the presence of excess collagen, was observed in an equivalent number of tissue sections in Treatment Group 1 (standard treatment), Treatment Group 2 (no chondroitin sulfate in the hydrogel), Treatment Group 3 (no poly L lysine in the hydrogel), Treatment Group 5 (no tetracycline in the hydrogel), and Treatment Group 7 (no trypsin in the Primer solution). Treatment group 4 (no chondroitin sulfate and no ploy L lysine in the hydrogel), Treatment Group 6 (no RPMI 1640 in the washout out or hydrogel), and Treatment Group 8 (No trypsin, and no CS, PLL, or tetracycline) had substantially fewer sections with collagen than standard treatment.

The collagen at treatment sites was scored as being either immature and poorly organized, or mature and well organized. Treatment Group 1 (standard treatment), Treatment Group 3 (no poly L lysine in the hydrogel), and Treatment Group 7 (no trypsin in the Primer solution) all had mature, organized collagen at the majority of treatment sites. Treatment Group 2 (no chondroitin sulfate in the hydrogel), Treatment Group 5 (no tetracycline in the hydrogel) and Treatment Group 6 (no RPMI 1640 in the Washout or hydrogel) had somewhat less mature collagen at treatment sites. Treatment Group 4 (no CS and no PLL in the hydrogel) and Treatment Group 8 (No trypsin in the Primer, and no CS, PLL, or tetracycline in the hydrogel) had immature collagen at treatment sites.

Standard treatment, and Treatment Group 6 (no RPMI 1640 in the Washout or hydrogel) were associated with mild to moderate mononuclear cell infiltrates consisting of lymphocytes and mononuclear cells surrounding sites of treatment. Inflammatory mononuclear infiltrates were somewhat more exuberant in Treatment Groups 2 (no chondroitin sulfate in the hydrogel), 3 (no poly L lysine in the hydrogel), 4 (no CS and no PLL in the hydrogel), 7 (no trypsin in the Primer solution), and 8 (no trypsin in the Primer, and no CS, PLL, or tetracycline in the hydrogel). Acute inflammatory infiltrates, consisting of neutrophils with associated abscesses, were observed in Treatment Group 5 (no tetracycline in the hydrogel).

Moderate fibroblast proliferation was apparent at all treatment sites, except those of Treatment Groups 4 (no CS and no PLL in the hydrogel) and 8 (No trypsin in the Primer, and no CS, PLL, or tetracycline in the hydrogel), where fibroblast proliferation was described as mild in most tissue section.

Histological evidence of microabscess formation was apparent in multiple sections from Treatment Group 5 (no tetracycline in the hydrogel), in 2 sections from Treatment Group 8 (No trypsin in the Primer, and no CS, PLL, or tetracycline in the hydrogel), and in one section from Treatment Groups 2 (no chondroitin sulfate in the hydrogel) and 7 (no trypsin in the Primer solution).

Proteinaceous material consistent with residual hydrogel was detected microscopically at 5 sites in tissue sections from standard treatment animals. Treatment Groups 4 and 8 had only one site each with apparent residual hydrogel, while Treatment Groups 3 and 7 had 7 sites each with residual hydrogel. Other treatment groups had variable amounts of residual hydrogel detected.

Accordingly, standard BLVR treatment including trypsin Primer solution, RPMI 1640 Washout solution, and fibrin hydrogel containing chondroitin sulfate, poly L lysine, and tetracycline was Well tolerated clinically and produced localized scarring reactions at the majority of treatment sites. After 4 weeks, most treatment sites displayed mature collagen in association with proliferating fibroblasts and a mild mononuclear cell infiltrate.

Under these experimental conditions, both CS and PLL contributed to the biological effectiveness of the treatment. Removal of either CS or PLL resulted in a small but consistent decrement in the number of sites demonstrating scar formation, and in the equality of collagen at those sites. Removal of both CS and PLL (Treatment Group 4) was associated with a marked reduction in both the number of responses and the quality of responses. The lack of efficacy displayed in Treatment Group 4 further indicates that tetracycline (at the concentrations used in this study) does not, by itself, promote scar formation by acting as a sclerosing agent. Removal of tetracycline from the hydrogel was associated with abscess formation in these experiments.

Removal of RPMI 1640 from the Washout and Hydrogel, and substitution with phosphate buffered saline (PBS) reduced the effectiveness of the procedure in these experiments. The number of treatment sites displaying scar formation, and the quality of collagen at those sites was reduced compared to standard therapy.

In these experiments, the use of a fibrinogen/thrombin gel without additives or trypsin pre-treatment, to function as a "biological glue" was associated with very limited scar formation, poorly formed collagen at those few sites where scar was initiated, and micro-abscesses. In these experiments, the elimination of trypsin Primer was associated with no reduction in the number of sites displaying evidence of scar formation at 4 weeks. Sites demonstrated mature collagen, similar to standard treatment. Residual hydrogel was present to a greater extent than standard treatment, and giant cells were noted at sites of treatment, consistent with a mild foreign body reaction.

Example 5

Evaluating Certain Lung Volume Reduction Methods and Compositions

In this example, ten different types of BLVR test treatments were examined, and compared to a standard BLVR treatment which served as a control. Test treatments differed from standard treatment in that one or more specific system components were removed.

Each test treatment was evaluated in 2 healthy sheep at 12 sites distributed throughout both lungs. All BLVR treatments were delivered using a dual lumen catheter system in identical fashion. BLVR treatment at each site required approximately 6-7 minutes to complete, and the entire 12-treatment procedure required approximately 90 minutes to complete. Follow-up studies were performed at 6 weeks.

Animals underwent baseline CT imaging and lung volume measurements by helium dilution. After 6 weeks of clinical monitoring, animals had a final set of studies performed, and were autopsied. Tissue samples were processed for histopathology as described herein.

Table 2 shows the different treatment conditions for the different experimental groups.

TABLE 2

Treatment Conditions

| Group | Animals/Group | Primer | Washout | Hydrogel | Follow-Up Period |
|---|---|---|---|---|---|
| 1. Control | 2 | Standard | Standard | Standard | 6 weeks |
| 2. No washout | 2 | Standard | None | Standard | 6 weeks |
| 3. 10X TCN | 2 | Standard | Standard | 10X TCN | 6 weeks |
| 4. 10X PLL | 2 | Standard | Standard | 10X PLL | 6 weeks |
| 5. 10X CS | 2 | Standard | PBS | 10X CS | 6 weeks |
| 6. 10X PLL&CS | 2 | Standard | Standard | 10X PLL&CS | 6 weeks |
| 7. 10X Trypsin | 2 | 10X Tryp. | Standard | Standard | 6 weeks |
| 8. Collagenase Primer | 2 | Replace Tryp. with Coll. | Standard | Standard | 6 weeks |
| 9. ½ Fibrinogen | 2 | Standard | Standard | 1.5% fibrinogen | 6 weeks |
| 10. No RPMI | 2 | Standard | PBS + Glucose | PBS + Glucose replacing RPMI | 6 weeks |
| 11. Tween 40 Primer | 2 | Replace Tryp. with Tween | Standard | Standard | 6 weeks |

In this experiment, the standard primer solution was 0.25% trypsin and 0.03% EDTA in PBS. The standard washout solution was 1× RPMI 1640. The standard hydrogel was 3% fibrinogen, 0.1% poly-L-lysine (PLL) (75-150,000 MWt), 0.1% chondroitin sulfate (CS) (50,000 Mwt), and 0.15% tetracycline (TCN) disolved in RPMI 1640. 10 ml of this solution was mixed with 1 ml of 1,000 units of thrombin in 40 mM $CaCl_2$. for in situ polymerization. In certain groups, one or more components were administered at a concentration 10 times that of the standard solution (indicated as 10× in Table 2 above). For example, a solution with 10× PLL contains 1% poly-L-lysine, a solution with 10× PLL&CS contains 1% poly-L-lysine and 1% chondroitin sulfate, etc.

The two test animals in Group 8 (0.25% collagenase Primer solution) experienced severe respiratory distress upon discontinuation of anesthesia following completion of treatment. Both animals were euthanized and autopsied. Both test animals in Group 4 (10× Poly-L-Lysine) recovered slowly from treatment, and demonstrated a depressed clinical status, and mildly abnormal breathing patterns for the first 8 hours thereafter. However, both animals had returned to normal baseline activity levels, and demonstrated normal breathing patterns after 12 hours. Activity levels, vital signs, eating patterns, and body weights remained normal in these two animals throughout the remainder of the study.

There were no signs of clinical distress, alterations from baseline activity level, or changes in eating patterns in any of the test groups to suggest an adverse clinical response to any of the other 9 treatments. For all animals except those in Group 8, body weights did not change from pre-treatment baseline values during the course of the study. Heart rate did not change from pre-treatment baseline values. Body temperature did not change from pre-treatment baseline values. Respiratory rates did not change from pre-treatment baseline values.

The percentage change in lung volume from baseline measured at 6 weeks following BLVR was evaluated. Group responses ranged from a 22% reduction to a 13% increase in volume. The largest reduction occurred in treatment Group 6 (10× PLL&CS). Standard treatment was associated with a mean 3.6% reduction in volume.

CT Image Assessment of BLVR Responses:

CT responses to BLVR treatment were assessed in two ways. The average number of sites per group showing evidence of a scar was determined, and a CT response score was generated. The CT response score is a semi-quantitative scoring system intended to assess the extent and organization of scarring on CT. Scores were assigned using a simple grading system based on an analysis of a CT image (0=the site appears the same as adjacent lung tissue with no evidence of treatment; 1=the site displays a focal increase in density but does not show a focal, linear, peripheral scar; 2=the site displays a focal, organizing scar with some highly dense areas, and other loosely organized areas; and 3=the site displays a focal, dense, organized peripheral scar).

For each animal, the average number of sites responding to treatment was determined by adding the total number of sites showing evidence of scarring in both animals in a treatment group, and dividing by 2. The maximum score that can be attained is 12, and the lowest is 0.

The CT response score for an animal was determined by adding up the scores for each treatment site, and dividing by 12. Final scores were generated as an average of the scores reported by three independent reviewers. The maximum possible CT response score that can be assigned using this scoring system is a 3 and the lowest is a 0.

Treatment Group 6 (10× PLL&CS) demonstrated the most consistent responses. Scarring, evident as a localized zone of increased density, was observed at a majority of sites. The lesions were of high density, suggesting mature scarring. Treatment Groups 4 (10× PLL), 5 (10× CS), and 7 (10× Trypsin) also demonstrated consistent scar formation, although lesions appeared less consistently, and were less dense in appearance than those of Treatment Group 6. The standard treatment demonstrated responses similar to those expected under the control conditions.

None of the animals demonstrated evidence of abscess formation, pleural effusion, or mediastinal lesions on CT images.

Necropsy Assessment of BLVR Responses:

In addition, a semi-quantitative scoring system was developed to assess the extent and organization of scar formation observed visually on the visceral pleural surface at the time of autopsy as an index of treatment success. Scores were assigned using a simple grading system based on a visual analysis (0=no visible scar is present at the treatment site; 1=a poorly-organized scar, or pleural bleb is present at the site of treatment; and 2=a well-organized scar with puckering of the pleura indicating volume reduction is present at the site of treatment).

For each animal, a total score was determined by adding up the scores for each treatment site. A final score was determined as the sum of the individual scores for the two animals in each group. The maximum possible score that can be assigned using this scoring system is a 24 and the lowest is a 0.

Responses to treatment, assessed grossly in terms of both the number of scars observed, and their extent of organization, ranged from 4.5 (Treatment Group 10, no RPMI) to 16.5 (Treatment Group 6, 10× PLL & CS). The most remarkable scarring responses were observed in Treatment Group 3 (10× TCN) with an average score of 12, Treatment Group 4 (10× PLL) with an average score of 13, Treatment Group 5 (10× CS) with an average score of 11.5, Treatment Group 6 (10× PLL & CS, ) with an average score of 16.5, and Treatment Group 7 (10× Trypsin) with an average score of 14.5. Standard treatment was associated with an intermediate response, with an average score of 8.5.

Additional necropsy findings included: i) acute hemorrhagic necrosis extending to the visceral pleura, and in one instance, through the visceral pleura (resulting in a hemothorax), in animals in treatment Group 10 (Collagenase Primer 0.25%) at necropsy performed within 8 hours of treatment administration; ii) two 2-3 cm diameter encapsulated, walled-off necrotic subpleural collections in treatment Group 3 animals (10× TCN) without evidence of associated purulence at 6 weeks; and iii) substantial amounts of localized, subpleural, residual hydrogel at sites treated with primer solution containing 2.5% Tween 40 at 6 weeks (in three instances, 1-2 cm diameter subpleural collections of necrotic debris were apparent within the parenchyma beneath an overlying pleural scar).

Accordingly, methods and devices of the invention are useful for disrupting the epithelial surface in a region of the distal lung of a patient in order to facilitate and/or improve the efficiency of the process of achieving non-surgical lung volume reduction. In some embodiments, aspects of the invention involve administering, to a region of a patient's lung, a composition that damages one or more epithelial cells and/or other cell types in the region contacted by the composition. In some embodiments, aspects of the invention involve administering, to a region of a patient's lung, an adhesive composition. Aspects of the invention also may include administering a growth factor to a region of a patient's lung. Embodiments of the invention also may involve collapsing a region of a patient's lung either by administering an antisurfactant composition or by a mechanical method or a combination thereof. Compositions of the invention (including, but not limited to, cell-disrupting, adhesive, growth factor, and wash/rinse solutions, or any combination thereof) may be prepared in PBS. Compositions of the invention (including, but not limited to, cell-disrupting, adhesive, growth factor, and wash/rinse solutions, or any combination thereof) also may be prepared in a balanced salt solution (including, but not limited to, Earl's, Hank's, or Eagle's balanced salt solutions). Compositions of the invention (including, but not limited to, cell-disrupting, adhesive, growth factor, and wash/rinse solutions, or any combination thereof) may be prepared in a buffer at physiological pH. In one aspect of the invention, compositions described in terms of % content may be % weight. In another aspect of the invention, compositions described in terms of % content may be % volume. A composition of the invention (including, but not limited to, cell-disrupting, adhesive, growth factor, and wash/rinse compositions, or any combination thereof) may be provided in a kit as a solution, a gel, a foam, a precipitate, a powder, a solid, a lyophilized preparation, a spray, or other form. A kit may contain two or more compositions in different forms. Similarly, a composition of the invention (including, but not limited to, cell-disrupting, adhesive, growth factor, and wash/rinse compositions, or any combination thereof) may be administered to a patient as a solution, a gel, a foam, a precipitate, a powder, a solid, a lyophilized preparation, a spray, or other form. Methods of the invention can be used to damage cells in the peripheral airways and/or the alveoli. Methods of the invention may include administering two or more compositions in different forms.

A number of embodiments of the invention have been described. Nevertheless, it will be understood that various modifications may be made without departing from the spirit and scope of the invention. Accordingly, other embodiments are within the scope of the claims and equivalents thereof.

The contents of all references, published patent applications and patents cited throughout the present application, including U.S. Pat. No. 6,610,043 issued on Aug. 26, 2003 and U.S. Pat. No. 6,682,520 issued on Jan. 27, 2004, are hereby incorporated by reference in their entirety.

I claim:

1. A method for non-surgical lung volume reduction, the method comprising applying an amount of energy with a catheter to a diseased alveolar region of the lung of a patient having emphysema, wherein the amount of energy is sufficient to damage the epithelial cells and the epithelial barrier within the diseased alveolar region of the lung and collapse at least a portion of said region thereby reducing the lung volume.

2. The method of claim 1, wherein the energy comprises thermal energy and is applied as heat.

3. The method of claim 2, wherein the catheter transfers heat to the alveolar region.

4. The method of claim 1, wherein the energy comprises ultrasonic energy.

5. The method of claim 4, wherein the catheter transmits the ultrasonic energy to the alveolar region.

6. The method of claim 1, wherein the energy comprises electrical energy.

7. The method of claim 6, wherein the catheter transmits the electrical energy to the alveolar region.

* * * * *